US006161042A

United States Patent [19]
Hartley et al.

[11] Patent Number: 6,161,042
[45] Date of Patent: Dec. 12, 2000

[54] RATE ADAPTIVE CARDIAC RHYTHM MANAGEMENT DEVICE USING TRANSTHORACIC IMPEDANCE

[75] Inventors: Jesse W. Hartley, Lino Lakes, Minn.; Marc H. Cohen, Baltimore, Md.; Nicholas J. Stessman, Minneapolis, Minn.; Scott A. Reedstrom, Vadnais Heights, Minn.; Steven D. Check, Eden Prairie, Minn.; James P. Nelson, Shoreview, Minn.

[73] Assignee: Cardiac Pacemakers, Inc., St. Paul, Minn.

[21] Appl. No.: 09/316,690

[22] Filed: May 21, 1999

Related U.S. Application Data

[62] Division of application No. 09/032,731, Feb. 27, 1998, Pat. No. 6,076,015.

[51] Int. Cl.[7] .................................................. A61N 1/365
[52] U.S. Cl. ............................... 607/20; 607/28; 600/547
[58] Field of Search ................................. 607/9, 17, 20, 607/28; 600/547

[56] References Cited

U.S. PATENT DOCUMENTS

| | | | |
|---|---|---|---|
| 4,596,251 | 6/1986 | Plicchi et al. ............................. | 128/419 |
| 4,686,987 | 8/1987 | Salo et al. ................................ | 128/419 |
| 4,702,253 | 10/1987 | Nappholz et al. ................ | 128/419 PG |
| 4,722,351 | 2/1988 | Phillipps et al. ......................... | 128/696 |
| 4,781,201 | 11/1988 | Wright et al. . | |
| 4,858,611 | 8/1989 | Elliott ..................................... | 128/419 |
| 4,901,725 | 2/1990 | Nappholz et al. ....................... | 128/419 |
| 4,966,146 | 10/1990 | Webb et al. ............................. | 128/419 |
| 5,027,813 | 7/1991 | Pederson et al. ........................ | 128/419 |
| 5,063,927 | 11/1991 | Webb et al. ...................... | 128/419 PG |
| 5,074,303 | 12/1991 | Hauck et al. ............................ | 128/419 |
| 5,085,215 | 2/1992 | Nappholz et al. ....................... | 128/419 |
| 5,137,019 | 8/1992 | Pederson et al. ........................ | 128/419 |
| 5,156,147 | 10/1992 | Warren et al. ........................... | 128/419 |
| 5,190,035 | 3/1993 | Salo et al. ............................... | 128/419 |
| 5,197,467 | 3/1993 | Steinhaus et al. ....................... | 128/419 |
| 5,201,808 | 4/1993 | Steinhaus et al. ....................... | 128/419 |
| 5,235,976 | 8/1993 | Spinelli .................................... | 607/25 |
| 5,249,572 | 10/1993 | Bonnet .................................... | 607/20 |

(List continued on next page.)

FOREIGN PATENT DOCUMENTS

| | | |
|---|---|---|
| 0003567 | 8/1979 | European Pat. Off. .......... A61B 5/04 |
| 447024 | 9/1991 | European Pat. Off. . |
| 702977 | 3/1996 | European Pat. Off. . |
| 765632 | 4/1997 | European Pat. Off. . |
| 28 05 482 | 2/1978 | Germany . |
| 9406512 | 3/1994 | WIPO . |

OTHER PUBLICATIONS

Hauck, J.A., "A Minute Ventilation Sensor Derived from Intra–thoracic Electric Impedance as a Cardiac Pacemaker Rate Modulator", *Ph.D. thesis, University of Minnesota* (Jun. 1993). iii, 80–85, 97,.

Jackson, L.B., "Digital Filters and Signal Processing", Second Edition, published by Kluwer Academic Publishers, 297–340, (Jun. 1996).

*Primary Examiner*—Kennedy Schaetzle
*Attorney, Agent, or Firm*—Schwegman, Lundberg, Woessner & Kluth, P.A.

[57] ABSTRACT

A cardiac rhythm management (CRM) device detects transthoracic impedance, extracts ventilation or other information, and adjusts a delivery rate of the CRM therapy accordingly. A four-phase sequence of alternating direction current pulse stimuli is periodically delivered to a patient's thorax. A transthoracic impedance signal is extracted using a weighted demodulation. Signal processing extracts ventilation information and removes cardiac stroke information using an adaptive lowpass filter. The adaptive filter cutoff frequency is based on the patient's heart rate; a higher cutoff frequency is provided for higher heart rates. Peak/valley detection indicates tidal volume, which is integrated to extract minute ventilation (MV). Short and long term averages are formed and compared to establish a MV indicated rate. Rate adjustment ignores MV information when a noise-measurement exceeds a threshold. An interference avoidance circuit delays delivery of the stimuli when telemetry pulses or other interfering signals are detected.

45 Claims, 10 Drawing Sheets

U.S. PATENT DOCUMENTS

| | | | |
|---|---|---|---|
| 5,271,395 | 12/1993 | Wahlstrand et al. | 607/9 |
| 5,273,034 | 12/1993 | Nilsson | 607/18 |
| 5,284,136 | 2/1994 | Hauk et al. | 607/24 |
| 5,303,702 | 4/1994 | Bonnet et al. | 607/20 |
| 5,318,597 | 6/1994 | Hauck et al. | 607/20 |
| 5,379,776 | 1/1995 | Murphy et al. | 128/705 |
| 5,391,190 | 2/1995 | Pederson et al. | 607/23 |
| 5,423,870 | 6/1995 | Olive et al. | 607/18 |
| 5,441,524 | 8/1995 | Rueter et al. | 607/18 |
| 5,507,785 | 4/1996 | Deno | 607/24 |
| 5,524,632 | 6/1996 | Stein et al. | 128/733 |
| 5,562,711 | 10/1996 | Yerich et al. | 607/17 |
| 5,562,712 | 10/1996 | Steinhaus et al. | 607/20 |
| 5,626,622 | 5/1997 | Cooper | 607/18 |
| 5,800,470 | 9/1998 | Stein et al. | 607/20 |
| 5,817,135 | 10/1998 | Cooper | 607/17 |
| 5,817,136 | 10/1998 | Nappholz | 607/17 |
| 5,824,020 | 10/1998 | Cooper | 607/17 |
| 5,824,029 | 10/1998 | Weijand et al. . | |

RATE ADAPTIVE CARDIAC RHYTHM MANAGEMENT DEVICE USING TRANSTHORACIC IMPEDANCE

This application is a divisional of application Ser. No. 09/032,731, filed Feb. 27, 1998, now U.S. Pat. No. 6,076,015.

TECHNICAL FIELD OF THE INVENTION

This invention relates generally to cardiac rhythm management devices and methods and particularly, but not by way of limitation, to a rate adaptive cardiac rhythm management device using transthoracic impedance information, such as a minute ventilation signal, to control the rate at which pacing therapy is delivered to a patient's heart.

BACKGROUND OF THE INVENTION

Pacemakers and other cardiac rhythm management devices deliver cardiac therapy to a patient's heart to assist in obtaining a rhythm of heart contractions that maintains sufficient blood flow through the patient's circulatory system under a variety of conditions. In particular, rate-adaptive pacemakers deliver electrical pacing pulses to stimulate contractions of the heart. The rate at which the pulses are delivered is adjusted to accommodate a metabolic need of the patient. During exercise, higher pacing rates are delivered, while lower pacing rates are delivered when the patient is at rest.

Different parameters are used as an indication of the patient's metabolic need for pacing therapy, including: blood pH, blood temperature, electrocardiogram (ECG) artifacts such as QT interval, blood oxygen saturation, breathing rate, minute ventilation, etc. Pacemakers include specific control algorithms for tracking the parameter indicating metabolic need, and providing a control signal for adjusting the pacing rate accordingly. A variety of difficulties exist that complicate sensing of the parameter indicating metabolic need and controlling the pacing rate.

For example, detecting blood pH encounters sensor stability problems. pH sensors may drift with age and time. Blood oxygenation saturation is measured using light emitters that complicate the lead system used to couple the pacemaker's pulse generator to the heart. Blood temperature is a poor indicator of metabolic need because of the long time lag between the onset of exercise and any detectable increase in blood temperature. ECG artifacts, such as QT interval, are difficult to detect in the presence of other myopotentials and motion artifacts. Breathing rate, also referred to as respiratory rate, is not particularly well correlated with the need for increased blood circulation. For example, it is possible for respiratory rate to increase while the patient is sleeping or talking.

Minute ventilation (also referred to as "minute volume" or "MV") is a respiratory-related parameter that is a measure of the volume of air inhaled and exhaled during a particular period of time. Minute ventilation correlates well with the patient's metabolic need for an increased heart rate over a range of heart rates. A minute ventilation signal can be obtained by measuring transthoracic (across the chest or thorax) impedance. Transthoracic impedance provides respiratory or ventilation information, including how fast and how deeply a patient is breathing. A component of transthoracic impedance varies as the patient inhales and exhales. Ventilation (e.g., breathing rate, which is also referred to as "ventilation rate" or "VR", and breathing volume, which is also referred to as "tidal volume" or "TV") information is included in the impedance signal. A minute ventilation signal (also referred to as "minute volume" or "MV") signal is derived from the impedance signal, as illustrated by Equation 1. MV measures air flow rate (e.g., liters per minute), TV measures volume per breath (e.g., liters per breath), and VR measures breathing rate (e.g., breaths per minute).

$$MV = TV \times VR \qquad (1)$$

A larger MV signal indicates a metabolic need for an increased heart rate, and the pacing rate can be adjusted accordingly by a cardiac rhythm management device. For example, one approach for measuring transthoracic impedance is described in Hauck et al., U.S. Pat. No. 5,318,597 entitled "RATE ADAPTIVE CARDIAC RHYTHM MANAGEMENT DEVICE CONTROL ALGORITHM USING TRANS-THORACIC VENTILATION," assigned to the assignee of the present application, the disclosure of which is incorporated herein by reference. However, many problems must be overcome to provide the most effective cardiac rhythm management therapy to the patient in a device that can remain implanted in the patient for a long period of time before requiring a costly surgical explantation and replacement procedure.

First, ventilation information included in the transthoracic impedance signal is confounded with a variety of extraneous signals that makes the ventilation information difficult to detect. For example, as the heart contracts during each cardiac cycle, its blood volume changes, contributing to a significant change in the transthoracic impedance signal that is unrelated to the ventilation information. The change in the transthoracic impedance signal due to blood volume changes resulting from heart contractions is referred to as cardiac "stroke volume" or "stroke" signal. Moreover, the frequencies of the heart contractions (e.g., 1–3 Hz) are extremely close to the frequency of the patient's breathing (e.g., under 1 Hz). This complicates separation of the stroke signal and the ventilation signal.

Furthermore, the frequency of the stroke and ventilation signals changes according to the patient's activity. For example, a resting patient may have a heart rate of 60 beats per minute and a ventilation rate of 10 breaths per minute. When exercising, the same patient may have a heart rate of 120 beats per minute and a ventilation rate of 60 breaths per minute. The changing frequencies of the stroke and ventilation signals further complicates the separation of these signals.

Another aspect of heart contractions also masks the ventilation signal. Heart contractions are initiated by electrical depolarizations (e.g., a QRS complex) resulting from paced or intrinsic heart activity. Such electrical heart activity signals may be detected during the measurement of transthoracic impedance. This further diminishes the accuracy of the transthoracic impedance measurement, and increases the difficulty of obtaining accurate ventilation information.

A further problem with certain other minute ventilation based cardiac rhythm management devices results from the use of a relatively high amplitude current pulse (e.g., 1 milliampere) to detect transthoracic impedance. Using high amplitude stimuli wastes power, risks capturing the heart (i.e., evoking a contraction), may trigger false detection of intrinsic heart activity by the pacemaker's sense amplifiers, and may produce a confusing or annoying artifact on electrocardiogram (ECG) traces or other diagnostic equipment.

Thus, there is a need for a cardiac rhythm management device that effectively manages the patient's heart rate based on an accurate indication of metabolic need. Such a cardiac rhythm management device must be sufficiently robust to operate in the presence of extraneous noise signals that confound the indication of metabolic need. There is a further need for such a device to operate at low power consumption, in order to maximize the usable life of the battery-powered implantable device.

SUMMARY OF THE INVENTION

The present invention provides, among other things, a method of determining transthoracic impedance in a cardiac rhythm management device. A multiple phase stimulus is repeatedly delivered to a thorax region of a patient. More than one phase of each multiple phase stimuli is demodulated to obtain sample points of a response signal including transthoracic impedance information.

In one embodiment, a response to each phase is sampled, weighted to obtain a filtering function, and combined. In another embodiment, a rate of delivering cardiac rhythm management therapy is adjusted based on ventilation information included in the transthoracic impedance information of a plurality of the sample points. In another embodiment, a noise-response function inhibits rate-adjustment if the transthoracic impedance signal is too noisy. In a further embodiment, a interference avoidance function delays delivery of the multiple phase stimulus to avoid simultaneous occurrence with an interfering signal (e.g., a telemetry signal).

Another aspect of the invention includes a method of determining transthoracic impedance in a cardiac rhythm management device that includes delivering stimuli to a thorax of the patient, sensing a response signal including transthoracic impedance information, attenuating a component of the response signal having frequencies above a lowpass cutoff frequency, and adaptively basing the lowpass cutoff frequency on a heart rate, and independent of a breathing rate signal, from the patient.

In one such embodiment, a cardiac stroke signal is attenuated to obtain ventilation information. The lowpass cutoff frequency is adaptively selected to be below the heart rate by selecting between a number of discrete lowpass cutoff frequencies, each lowpass cutoff frequency corresponding to a particular range of values of the heart rate.

In a further embodiment, the method includes detecting peaks and valleys of the response signal. Differences between peaks and valleys of the response signal provide tidal volume data points, which are integrated for a predetermined period of time to obtain minute ventilation data points. A rate of delivering cardiac rhythm management therapy is adjusted based on the minute ventilation data points. Alternatively, breath-by-breath minute ventilation data points are obtained. Instead of performing the integration, time differences between the peaks and valleys of the response signal provide respiration period data points corresponding to the tidal volume data points. The tidal volume data points are divided by the corresponding respiration period data points to obtain minute ventilation data points, upon which a rate of delivering cardiac rhythm management therapy is adjusted.

Another aspect of the present invention includes a cardiac rhythm management device. The device includes an exciter, adapted to be coupled to a thorax of a patient for repeatedly delivering a multiphase stimulus thereto. A signal processor includes a receiver for obtaining transthoracic impedance information responsive to the stimuli. A demodulator, included in the signal processor, includes sampling elements for demodulating the transthoracic impedance in response to different phases of the multiphase stimulus. A therapy circuit is adapted to be coupled to a heart of the patient for delivering cardiac rhythm management therapy thereto. A controller is coupled to the therapy circuit for adjusting a rate of delivery of the cardiac rhythm management therapy based on the transthoracic impedance.

In one embodiment, the device includes a noise-reversion circuit that inhibits rate-adjustment if the transthoracic impedance signal is too noisy. In a further embodiment, the device is included within a cardiac rhythm management system that also includes an endocardial lead, carrying first and second electrodes, and a housing including third and fourth electrodes.

Another aspect of the invention includes a cardiac rhythm management device that includes an exciter for delivering stimuli to a thorax. A signal processor includes a receiver for obtaining a transthoracic impedance responsive to the stimuli. The signal processor extracts ventilation information from the transthoracic impedance. The signal processor includes an adaptive lowpass filter for removing a cardiac stroke component of the transthoracic impedance signal. A cutoff frequency of the adaptive lowpass filter is adaptively based on a heart rate signal of the patient.

The cutoff frequency of the adaptive lowpass filter is independent of a breathing rate signal from the patient. A therapy circuit is adapted to be coupled to a heart of the patient for delivering cardiac rhythm management therapy thereto. A controller is coupled to the therapy circuit for adjusting a rate of delivery of the cardiac rhythm management therapy based on the ventilation information.

The present invention provides, among other things, a cardiac rhythm management system, device, and methods that sense transthoracic impedance and adjust a delivery rate of the cardiac rhythm management therapy based on information extracted from the transthoracic impedance. The present invention effectively manages the patient's heart rate based on an accurate indication of metabolic need. It provides robust operation in the presence of extraneous noise signals that confound the indication of metabolic need. It also provides low power consumption, increasing the usable life of the battery-powered implantable device. Other advantages will be apparent upon reading the following detailed description of the invention, together with the accompanying drawings which form a part thereof.

BRIEF DESCRIPTION OF THE DRAWINGS

In the drawings, like numerals describe substantially similar components throughout the several views.

DETAILED DESCRIPTION OF THE INVENTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

Electrode Configuration and Top-Level Block Diagram

Figure 1:
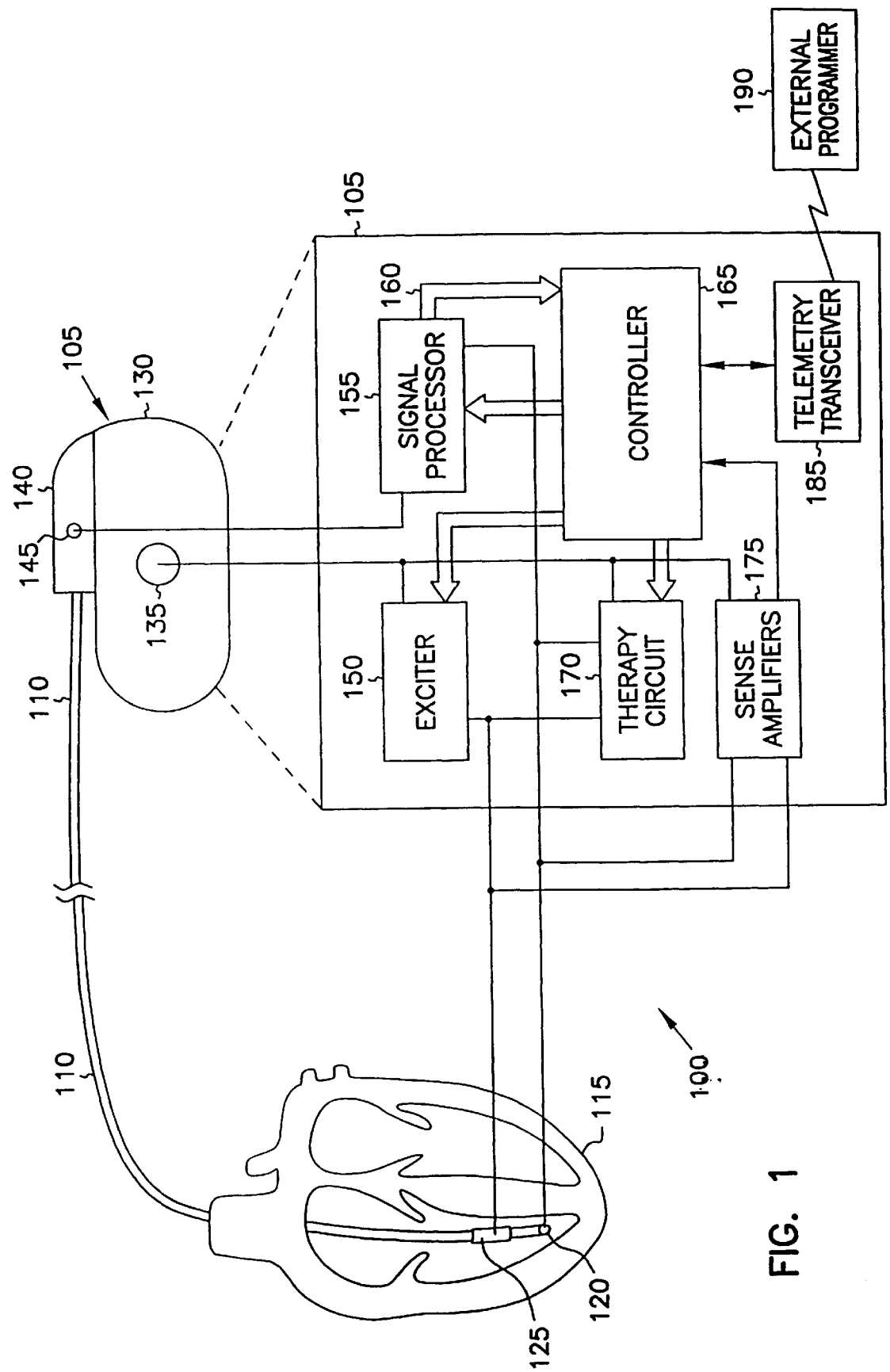
FIG. 1 is a schematic/block diagram illustrating generally one embodiment of a cardiac rhythm management system according to the present invention, including a cardiac rhythm management device and electrode connections.

FIG. 1 is a schematic/block diagram illustrating generally, by way of example, but not by way of limitation, one embodiment of a cardiac rhythm management system 100 according to the present invention. System 100 includes, among other things, cardiac rhythm management device 105 and leadwire ("lead") 110 for communicating signals between device 105 and a portion of a living organism, such as heart 115. Embodiments of device 105 include bradycardia and antitachycardia pacemakers, cardioverters, defibrillators, combination pacemaker/defibrillators, drug delivery devices, and any other cardiac rhythm management apparatus capable of providing therapy to heart 115. System 100 may also include additional components such as, for example, a remote programmer capable of communicating with device 105.

In one embodiment, system 100 is implantable in the living organism, such as in a pectoral or abdominal region of a human patient, or elsewhere. In another embodiment, portions of system 100 (e.g., device 105) are alternatively disposed externally to the human patient. In the illustrated embodiment, portions of lead 110 are disposed in the right ventricle, however, any other positioning of lead 110 is included within the present invention. For example, lead 110 may alternatively be positioned in the atrium or elsewhere. In one embodiment, lead 110 is a commercially available bipolar pacing lead. System 100 can also include other leads in addition to lead 110, appropriately disposed, such as in or around heart 115, or elsewhere.

In one embodiment, system 100 includes at least four electrodes, such as described in Hauck et al. U.S. Pat. No. 5,284,136 entitled "DUAL INDIFFERENT ELECTRODE PACEMAKER," assigned to the assignee of the present invention, the disclosure of which is incorporated herein by reference. It is understood, however, that the present invention also includes using a different number of electrodes (e.g., 2 or 3 electrodes, or more than 4 electrodes). In one example, a first conductor of multiconductor lead 110 electrically couples a first electrode, such as tip electrode 120 (e.g., disposed at the apex of the right ventricle of heart 115), to device 105. A second conductor of multiconductor lead 110 independently electrically couples a second electrode, such as ring electrode 125, to device 105. In one embodiment, device 105 includes a hermetically sealed housing 130, formed from a conductive metal, such as titanium. Housing 130 (also referred to as a "case" or "can") is substantially covered over its entire surface by a suitable insulator, such as silicone rubber, except for at a window that forms a third electrode, referred to as a "case" or "can" electrode 135. In one embodiment, a header 140 is mounted on housing 130 for receiving lead 110. Header 140 is formed of an insulative material, such as molded plastic. Header 140 also includes at least one receptacle, such as for receiving lead 110 and electrically coupling conductors of lead 110 to device 105. Header 140 also includes a fourth electrode, referred to as indifferent electrode 145.

FIG. 1 also illustrates generally portions of device 105, together with schematic illustrations of connections to the various electrodes. Device 105 includes an electrical stimulation source, such as exciter 150. Exciter 150 delivers an electrical excitation signal, such as a strobed sequence of current pulses or other measurement stimuli, to heart 115 (e.g., between ring electrode 125 and tip electrode 120, or using any other electrode configuration suitable for delivering the current pulses). In response to the excitation signal provided by exciter 150, a response signal is sensed by signal processor 155 (e.g., between tip electrode 120 and indifferent electrode 145, or any other suitable electrode configuration).

In one embodiment, the response signal sensed by signal processor 155 is a voltage that represents a transthoracic (i.e., across a portion of the chest or thorax) impedance. A minute ventilation signal (also referred to as "minute volume" or "MV") signal is derived from the impedance signal, as illustrated above by Equation 1. A larger MV signal indicates a metabolic need for an increased heart rate. According to one aspect of the invention, signal processor 155 extracts ventilation information, including the MV signal, from the impedance signal. Based on the MV signal, signal processor 155 outputs an indicated rate signal at node 160 to controller 165. Based on the indicated rate signal at node 160, controller 165 adjusts the rate of delivery of cardiac rhythm management therapy, such as electrical pacing stimuli, to heart 115 by therapy circuit 170. Such pacing stimuli includes, for example, providing bipolar pacing between tip electrode 120 and ring electrode 125, providing unipolar pacing between can electrode 135 and either of tip electrode 120 or ring electrode 125, or providing pacing stimuli using any other suitable electrode configuration.

Exciter and Resulting Stimuli Waveform

Figure 2:
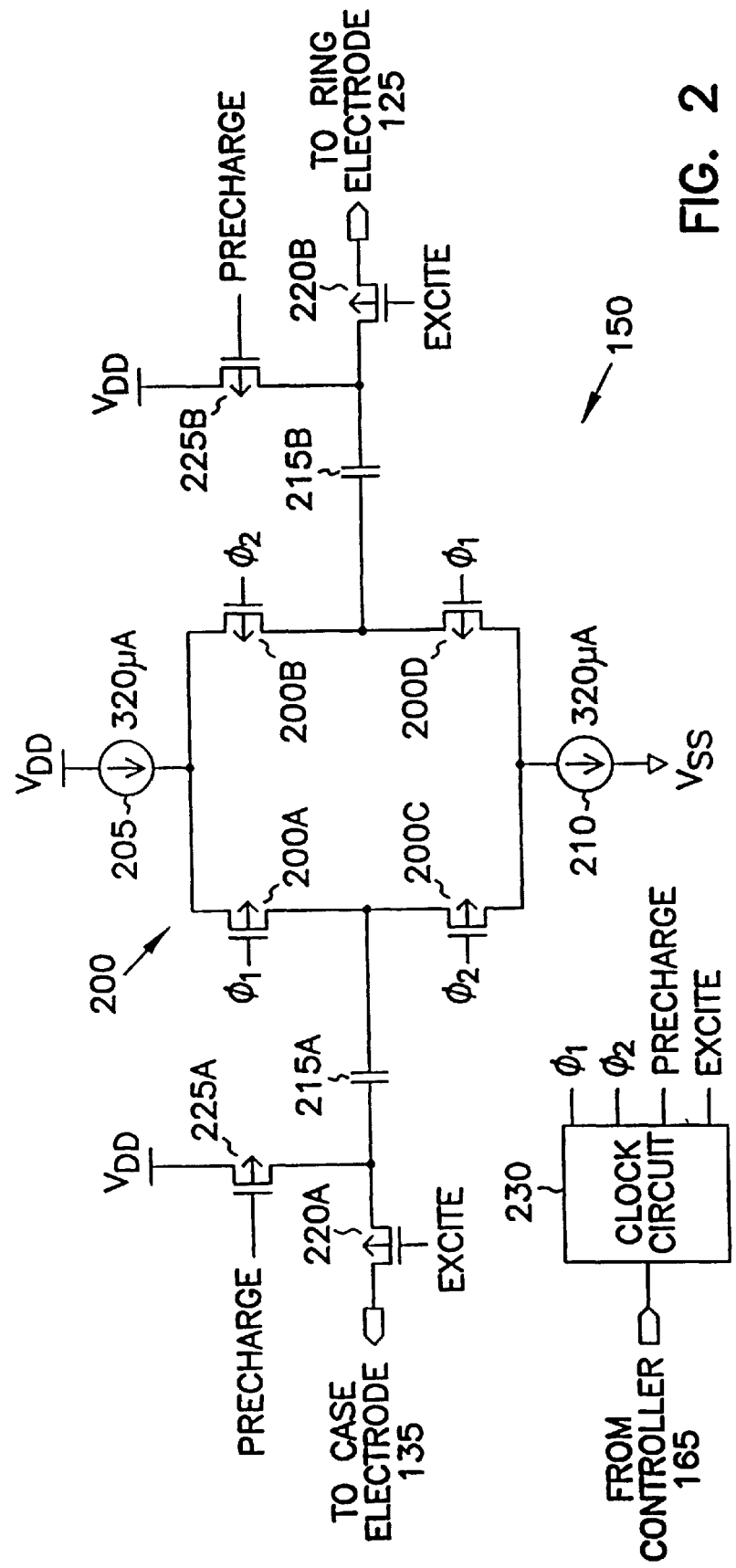
FIG. 2 is a schematic/block diagram illustrating generally one embodiment of particular circuits included within an exciter for delivering electrical excitation stimuli to a heart.

FIG. 2 is a schematic/block diagram illustrating generally, by way of example, but not by way of limitation, one embodiment of particular circuits included within exciter 150 for delivering electrical stimuli (e.g., strobed alternating-direction constant-amplitude current pulses) to heart 115. Exciter 150 includes, among other things, bridge switcher 200, comprising switches 200A, 200B, 200C, and 200D. In one embodiment, switches 200A–D are implemented as transistors, such as p-channel metal-oxide semiconductor (PMOS) field-effect transistors (FETs), or any other suitable switches.

Exciter 150 also includes current source 205 and current sink 210. In one embodiment, each of current source 205 and current sink 210 include transistors in a regulated cascode or other suitable configuration. In one embodiment, switcher 200 is electrically coupled to case electrode 135 and ring electrode 125 through respective dc blocking capacitors 215A and 215B and respective switches 220A and 220B (e.g., PMOS transistors). Switches 225A and 225B (e.g., PMOS transistors) precharge respective capacitors 215A and 215B. Exciter 150 also includes a clock circuit 230 receiving one or more clock or other control signals from controller 165 and providing signals to the control terminals of each of switches 200A–D, 220A–B, and 225A–B.

Figure 3:
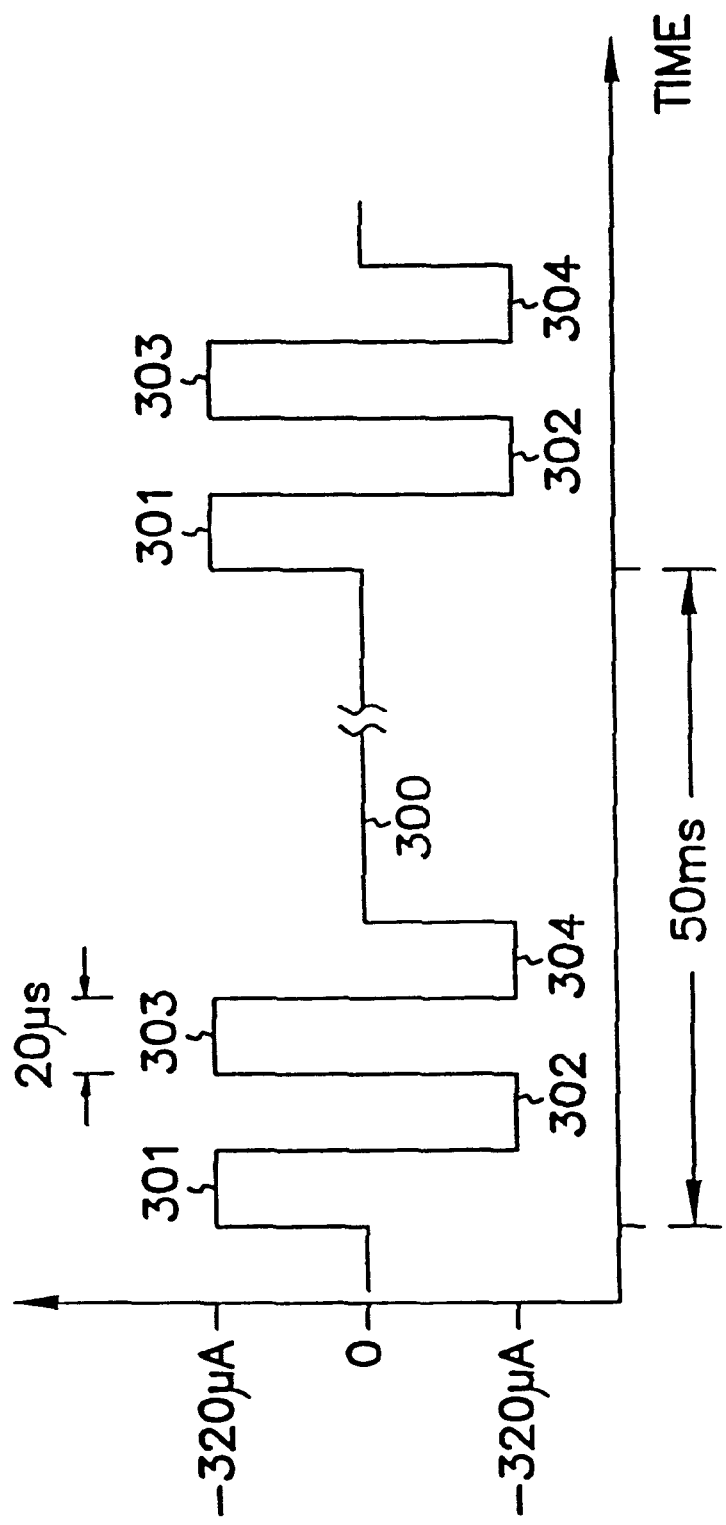
FIG. 3 illustrates generally a current waveform resulting from operation of an exciter according to one aspect of the present invention.

FIG. 3 illustrates generally a current waveform 300 between case electrode 135 and ring electrode 125 resulting from operation of exciter 150 according to one aspect of the present invention. According to one aspect of the invention, waveform 300 includes a multiple phase ("multiphase") stimulus. In one embodiment, the multiphase stimulus includes a square wave, such as four current pulses 301, 302, 303, and 304 in sequentially alternating polarity/direction, each current pulse being a phase of the multiphase stimulus. In one embodiment, by way of example, but not by way of limitation, each one of current pulses 301–304 has a duration that is selected at approximately between 1 and 100 microseconds (e.g., approximately between 2 and 60 microseconds, such as at 20 microseconds), to allow adequate sampling of the transthoracic impedance signal obtained in response thereto. In the embodiment illustrated in FIG. 3, pulses 301–304 form a square wave having a carrier frequency of approximately 25 kilohertz. Other suitable durations of current pulses 301–304 could also be used, providing a different resulting carrier frequency. According to another aspect of the invention, the sequence of current pulses 301–304 is strobed. In one embodiment, by way of example, but not by way of limitation, the four pulse sequence 301–304 is repeated at a strobing frequency (also referred to as a repetition frequency or a sampling frequency) of approximately 20 Hertz (i.e., a 50 millisecond time interval). Other suitable strobing/repetition frequencies could also be used. For example, but not by way of limitation, any strobing/repetition time interval shorter than 55 milliseconds could be used.

The amplitude of current pulses 301–304 was selected at less than approximately 1 milliampere. For example, approximately 320 microampere amplitude current pulses 301–304 provide an adequate excitation signal to obtain the desired response signal, while minimizing current drain of the implanted device 105, thereby increasing its implanted longevity. However, other amplitudes of current pulses 301–304 could also be used. Such amplitudes of current pulses 301–304 should be less than the tissue stimulation threshold of the heart to avoid any resulting cardiac depolarization. The strobing frequency is sufficiently fast to provide adequate sampling of ventilation or other information carried by the transthoracic impedance signal obtained in response to the electrical stimuli provided by exciter 150. Such ventilation information can appear at frequencies as high as approximately 1 Hertz, depending on the patient's breathing rate. The strobing frequency also minimizes aliasing of a "stroke volume" component of the transthoracic impedance signal (i.e., a portion of the transthoracic impedance signal that varies along with the patient's heartbeat instead of the patient's breathing rate). The stroke volume component of the transthoracic impedance signal can have frequencies as high as approximately 3 Hertz, depending on the patient's heart rate.

Prior to each sequence of current pulses 301–304, dc blocking capacitors 215A–B are precharged by a bias circuit, such as by turning on switches 200A–D and 225A–B, with switches 220A–B being off. Current source 205 and current sink 210 establish the operating point of a terminal of each of dc blocking capacitors 215A–B that is coupled to switcher 200. After precharging, switches 225A–B are turned off. Next, pulse 301 is produced by turning on switches 200A, 200D, and 220A–B, such that current delivered by current source 205 leaves case electrode 135. The current returns through ring electrode 125, and is sunk by current sink 210. Next, pulse 302 is produced by turning on switches 200B–C and 220A–B, such that current delivered by current source 205 leaves ring electrode 125. The current returns through case electrode 135, and is sunk by current sink 210. Next, pulse 303 is produced by again turning on switches 200A, 200D, and 220A–B, such that current delivered by current source 205 leaves case electrode 135. The current returns through ring electrode 125, and is sunk by current sink 210. Next, pulse 304 is produced by again turning on switches 200B–C and 220A–B, such that current delivered by current source 205 leaves ring electrode 125. The current returns through case electrode 135, and is sunk by current sink 210. Switches 220A–B, 200A–D, and 225A–B are turned off until precharging for another four current pulse sequence 301–304, which is delivered approximately 50 milliseconds later, as illustrated in FIG. 3.

According to one aspect of the invention, clock circuit 230 provides nonoverlapping control signals to switches 225A–B and switches 220A–B. As a result, switches 225A–B are not turned on at the same time as switches 220A–B. This avoids any coupling of either of case electrode 135 and ring electrode 125 to the positive power supply voltage $V_{DD}$.

Waveform 300 provides several important advantages allowing efficient and accurate sensing of the MV signal, allowing system 100 to provide more effective delivery of rate-responsive cardiac rhythm management therapy to the patient. First, system 100 allows the use of relatively low amplitude current pulses (e.g., +/–320 microamperes). This conserves power, allowing battery-powered portions of system 100 (e.g., device 105) to remain implanted in the patient for a longer usable lifetime. Because of their low amplitude, current pulses 301–304 do not produce any discernable artifacts on electrocardiogram (ECG) traces or on other diagnostic equipment. Such artifacts can confuse diagnosing physicians. The low amplitude current pulses 301–304 are also less likely to trigger false detection of intrinsic heart activity, such as by sense amplifiers included in device 105. False detection of intrinsic heart activity can inhibit proper delivery of pacing therapy, rendering cardiac rhythm management ineffective and increasing risk to the patient. According to one aspect of the present invention, the sensitivity setting of such sense amplifiers can be increased without being affected by interference from the current pulses 301–304 produced by exciter 150. Moreover, the low amplitude current pulses 301–304 avoid the risk of capturing heart 115 (i.e., inducing an electrical depolarization and heart contraction), particularly when current pulses 301–304 are delivered from small electrodes that are also used for delivering pacing therapy to heart 115.

According to another aspect of the invention, waveform 300 includes current pulses 301–304 that are strobed at a frequency of approximately 20 Hertz. The 25 kilohertz carrier frequency is only present for a short fraction of the 50 millisecond strobing time interval (i.e., duty cycle of less than 1%). The strobing also reduces power consumption and obtains increased implanted longevity of device 105, as described above.

Waveform 300 also provides balance in both amplitude and duration for each polarity/direction of the current pulses 301–304, thereby balancing the charge delivered to heart 115. Each +320 microampere pulse (e.g., 301 and 303) is balanced by an equal duration corresponding −320 microampere pulse (e.g., 302 and 304). This method of balancing the amplitude and duration of waveform 300 reduces the likelihood of capturing heart 115 or inducing false sensing as intrinsic heart activity sensed by device 105.

Interference Avoidance

In one embodiment, device 105 avoids delivering the multiphase stimulus in the presence of other interfering signals, such as telemetry signals, that increase the difficulty of accurately detecting a response. Referring again to FIG. 1, in one embodiment, device 105 includes a telemetry transceiver 185 for communicating via telemetry signals (e.g., telemetry pulses) with an external programmer 190, such as by inductively coupled coils in each of the device 105 and the external programmer 190. When telemetry pulses are detected by the telemetry receiver in device 105, and scheduled delivery of the multiphase stimulus coincides with the detection of the telemetry pulses, controller 165 delays delivery of the multiphase stimulus (e.g., current pulses 301–304), such as by approximately 1 millisecond. This avoids inaccuracies in the response signal to current pulses 301–304 that may result from the telemetry pulses or, similarly, from the presence of other interfering signals.

Signal Processor

Figure 4:
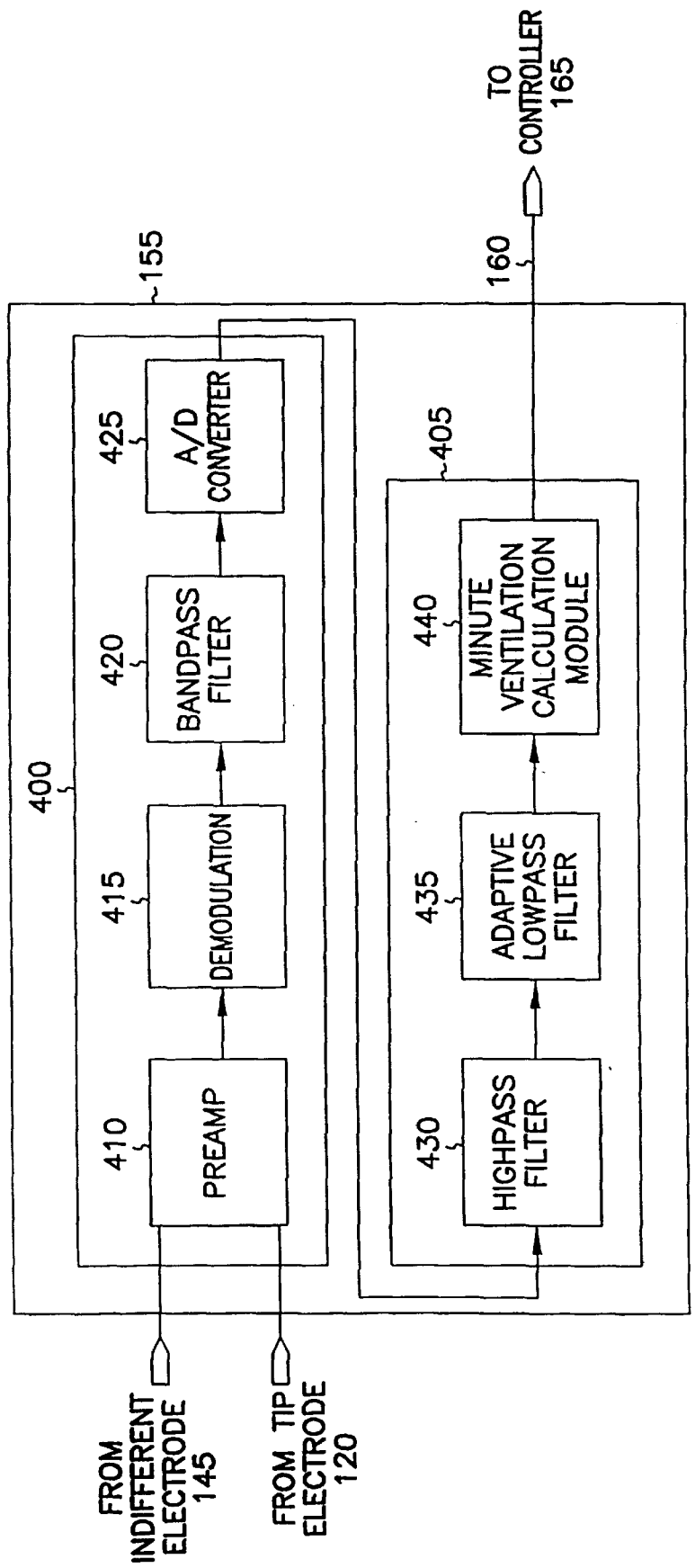
FIG. 4 is a block diagram illustrating generally one embodiment of portions of a signal processor.

FIG. 4 is a block diagram illustrating generally, by way of example, but not by way of limitation, one embodiment of portions of signal processor 155. Signal processor 155 includes analog signal processing circuit 400 and digital signal processing circuit 405. Inputs of a preamplifier 410 (also referred to as a preamp or a receiver) of analog signal processing circuit 400 are electrically coupled to each of indifferent electrode 145 and tip electrode 120 for receiving a signal in response to the above-described stimuli provided by exciter 150. Analog signal processing circuit 400 also includes demodulator 415, receiving the output of preamplifier 410, and providing an output signal to bandpass filter 420. An output signal from bandpass filter 420 is received by analog-to-digital (A/D) converter 425. An output signal from A/D converter 425 is received at highpass filter 430 of digital signal processing circuit 405.

In one embodiment, digital signal processing circuit 405 is included within controller 165 such as, for example, as a sequence of instructions executed by a microprocessor. In another embodiment, digital signal processing circuit 405 includes separately implemented hardware portions dedicated to performing the digital signal processing tasks described below. An output signal from highpass filter 430 is received by adaptive lowpass filter 435 of digital signal processing circuit 405. Minute ventilation calculation module 440 receives an output signal from adaptive lowpass filter 435, and provides a resulting indicated rate signal at node 160 to controller 165.

Preamplifier

Figure 5:
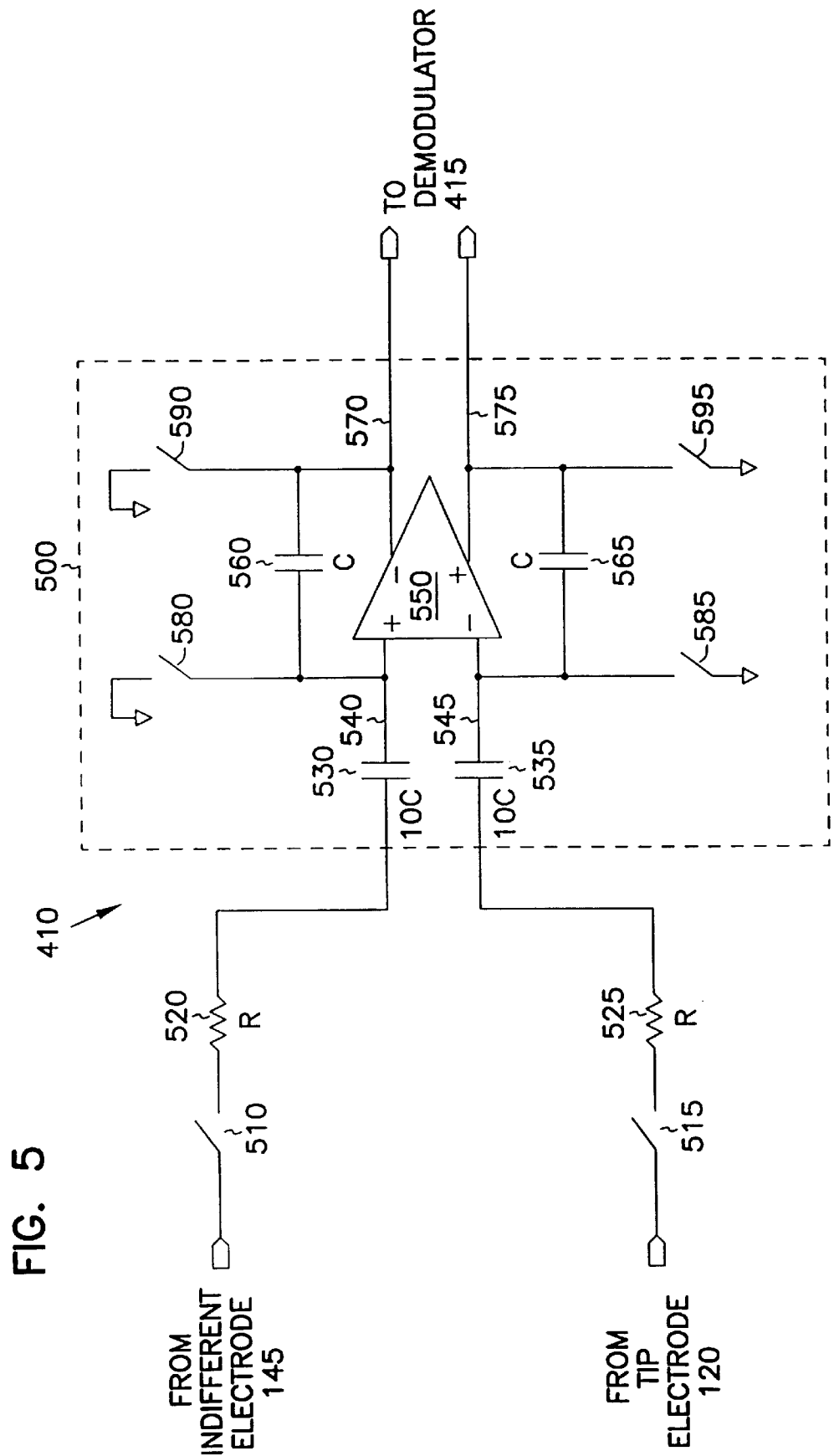
FIG. 5 is a schematic diagram illustrating generally one embodiment of a preamplifier.

FIG. 5 is a schematic diagram illustrating generally, by way of example, but not by way of limitation, one embodiment of preamplifier 410. Preamplifier 410 includes a switched-capacitor (SC) differential amplifier 500. Preamplifier 410 is electrically coupled to indifferent electrode 145 and tip electrode 120 through respective switches 510 and 515 and respective resistors 520 and 525. Switches 510 and 515 are turned on only during the approximate time when the stimuli current pulses 301–304 are being delivered by exciter 150. Resistors 520 and 525 provide antialiasing/bandlimiting of the input signals received from indifferent electrode 145 and tip electrode 120.

Differential amplifier 500 includes input capacitors 530 and 535, coupled to resistors 520 and 525 respectively, and also coupled to a respective positive input at node 540 and a negative input, at node 545, of a differential-input/differential-output operational amplifier 550. Feedback capacitors 560 and 565 are coupled from a respective negative output, at node 570, and a positive output, at node 575, of operational amplifier 550, to its respective positive input, at node 540, and negative input, at node 545. In one embodiment, input capacitors 530 and 535 have approximately 10 times the capacitance value of respective feedback capacitors 560 and 565.

Differential amplifier 500 also includes autozeroing input switches, 580 and 585, coupling respective input nodes 540 and 545 to respective reference voltages (e.g., a ground voltage). Autozeroing output switches 590 and 595 couple respective output nodes 570 and 575 to respective reference voltages (e.g., a ground voltage). Switches 580, 585, 590, and 595 provide zeroing of corresponding feedback capacitors 560 and 565. Switches 580 and 585 further establish the bias points of the input nodes 540 and 545 of operational amplifier 550, such as during sampling of signals from indifferent electrode 145 and tip electrode 120 onto input capacitors 530 and 535.

Preamplifier 410 receives a voltage based on the transthoracic impedance between indifferent electrode 145 and tip electrode 120. For example, a transthoracic impedance of 50 ohms results in a voltage between the inputs of differential amplifier 500 of approximately 16 millivolts. The transthoracic impedance varies as the patient breathes, increasing as air fills the patient's thoracic cavity during inspiration and decreasing as air is released during expiration. The transthoracic impedance may vary, for example, by approximately 2 ohms during respiration, resulting in an approximately 0.64 millivolt modulation of the approximately 16 millivolt baseline signal appearing between the inputs of differential amplifier 500. These impedance and voltage values are recited by way of example only; actual impedance and voltage values will vary according to, among other things, differences in patient anatomy and electrode placement.

In one embodiment of the invention, by way of example, but not by way of limitation, the electrodes used for delivering the excitation current (e.g., ring electrode 125 and case electrode 135) are different from the electrodes used for sensing the response thereto (e.g., indifferent electrode 145 and tip electrode 120). This advantageously reduces the magnitude of the baseline component of the transthoracic impedance signal, thereby increasing the relative contribution of the ventilation component of the transthoracic impedance signal, and increasing the signal-to-noise ratio (SNR). Alternatively, the same electrodes could be used for delivering the excitation current and sensing the response thereto.

In one embodiment, differential amplifier 500 provides an effective voltage gain of approximately 6. In the above example, the 16 millivolt baseline signal is amplified to approximately 100 millivolts by differential amplifier 500 and the resulting signal is provided to demodulator 415.

Demodulator

Demodulator 415 samples the signal obtained in response to current pulses 301–304 after the above-described amplification by preamplifier 410. According to one aspect of the invention, the output of preamplifier 410 is sampled at the end of each of current pulses 301–304. Demodulator 415 combines these four samples into a single value using a weighted average. The resulting weighted average represents the total impedance (i.e., including both baseline and ventilation components) obtained for the sequence of four current pulses 301–304.

In one embodiment, the weighted average is formed by weighting the second and third samples, obtained from respective current pulses 302 and 303, by a factor of approximately 3.0 relative to the first and fourth samples, obtained from respective current pulses 301 and 304. Weighting the samples advantageously provides an additional highpass filtering function, substantially transmitting the transthoracic impedance signal at the 25 kilohertz carrier frequency of the current pulses 301–304, while substantially rejecting out-of-band signals. In particular, demodulator 415 provides additional rejection of low-frequency signals, such as R-waves and other electrical signals produced by heart 115. A transfer function provided by one embodiment of demodulator 415, is described in the z-domain, as illustrated in Equation 2.

$$H(z)=0.219(z^{-3}-3z^{-2}+3z^{-1}-1) \quad (2)$$

In this embodiment, demodulator 415 provides a voltage gain that is approximately between 1.75 and 2.0 for the in-band transthoracic impedance signal. Moreover, demodulator 415 also advantageously attenuates signals at frequencies below 100 Hz by a factor of at least approximately 120 dB, including such signals as R-waves and other electrical intrinsic heart activity signals produced by heart 115, which can interfere with sensing the patient's transthoracic impedance.

Figure 6:
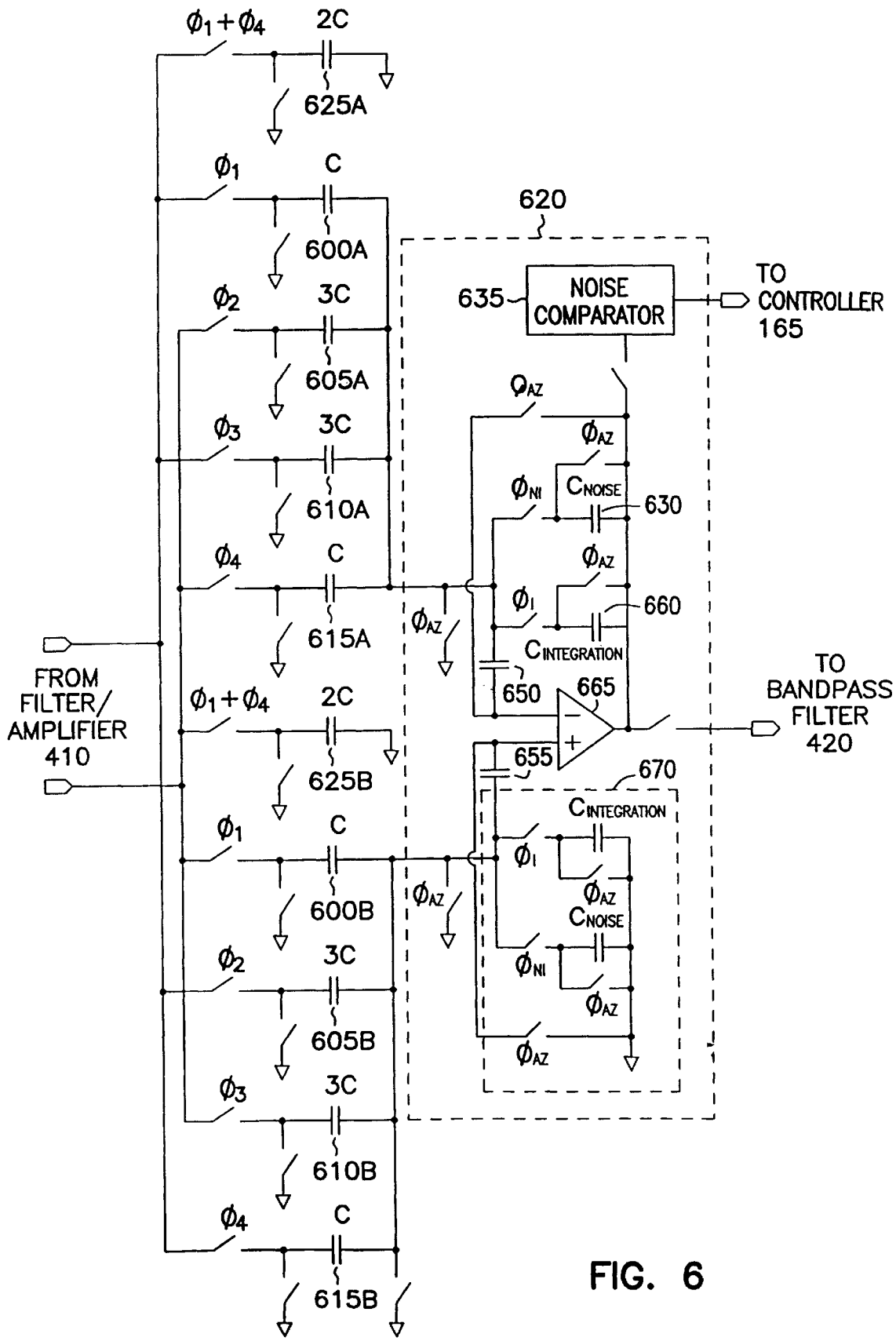
FIG. 6 is a schematic diagram illustrating generally one embodiment of a demodulator.

FIG. 6 is a schematic diagram illustrating generally, by way of example, but not by way of limitation, one embodiment of a switched-capacitor demodulator 415. The output signal from preamplifier 410 is sampled onto capacitors 600A–B in response to current pulse 301, onto capacitors 605A–B in response to current pulse 302, onto capacitors 610A–B in response to current pulse 303, and onto capacitors 615A–B in response to current pulse 304. Capacitors 605A–B and 610A–B provide 3 times the capacitance value of capacitors 600A–B and 615A–B, in order to provide the above-described weighting of the samples. After the weighted sampling of the output of preamplifier 410 in response to the four current pulses 301–304, these weighted samples are summed by switched-capacitor integrator 620 (also referred to as a summer).

Also illustrated in FIG. 6 are dummy capacitors 625A–B. Each of dummy capacitors 625A–B has a capacitance value that is twice that of one of capacitors 600A–B, and twice that of one of capacitors 615A–B. Dummy capacitors 625A–B are switched in during sample of current pulses 301 and 304. As a result, demodulator 415 presents the same load capacitance to preamplifier 410 during sampling of each of the four current pulses 301–304. As seen in FIG. 6, however, the charge that is sampled onto dummy capacitors 625A–B is not included in the weighted sample (i.e., the resulting charge is not included in the integration provided by integrator 620). Furthermore, it is understood that, in one embodiment, the capacitors illustrated in FIG. 6 are initialized (e.g., discharged) prior to sampling any particular sequence of current pulses 301–304.

In FIG. 6, integrator 620 includes input capacitors 650 and 655, which are autozeroed by switches, as illustrated, during the clock phase $\phi_{AZ}$. An integration capacitor 660, which is in the feedback path around operational amplifier 665, sums the weighted samples obtained in response to the four current pulses 301–304 during an integration clock phase $\phi_I$. A noise sampling/integration capacitor 630, which is also in the feedback path around operational amplifier 665, sums the weighted samples obtained in the absence of delivered current pulses during a noise integration clock phase $\phi_{NI}$, as described below. Integrator 620 also provides a matching network 670 on the other input of operational amplifier 665 for matching the above-described switched capacitor operation.

In one embodiment, demodulator 415 also provides a noise sensing mode of operation. In normal operation, demodulator 415 samples the output of filter/amplifier 410 in response to current pulses 301–304 provided by exciter 150. During a noise sensing mode of operation, exciter 150 is turned off (i.e., current pulses 301–304 are not provided), and demodulator 415 samples, onto switched-in noise sampling/integration capacitor 630, noise arising from external sources (e.g., heart signals or any environmental noise sources) and internal noise produced by circuits coupled to the input of the demodulator 415. In particular, demodulator 415 is capable of sensing noise that is at frequencies close to the 25 kilohertz carrier frequency of the current pulses 301–304.

In one embodiment, the gain of demodulator 415 is increased (e.g., by a factor of approximately 2.0–2.5) during noise sensing mode in order to provide more sensitive noise detection. For example, the noise sampling/integration capacitor 630 used during noise sensing is different in value from a corresponding integration capacitor used during normal operation of demodulator 415, in order to provide a different gain during noise sensing.

According to one aspect of the invention, device 105 also includes a noise reversion circuit based on the noise sensed by demodulator 415 when exciter 150 is turned off. A noise comparator 635 receives a signal derived from the output of demodulator 415. Comparator 635 determines whether the detected noise exceeds a particular programmable threshold value. If the detected noise exceeds the threshold value, subsequent circuits ignore the output of demodulator 415 (e.g., until the detected noise again falls below the threshold value). In one embodiment, the programmable threshold value used by comparator 635 is implemented as a programmable switched-capacitor array, providing threshold voltages ranging between approximately 4–120 millivolts at the output of demodulator 415 (corresponding to an impedance noise threshold between approximately 0.4–12 ohms).

Bandpass Filter

In one embodiment, bandpass filter 420 provides a passband between single pole corner frequencies at 0.1 Hz and 2.0 Hz, and includes a gain stage providing a voltage gain that is programmable (e.g., 6×, 12×, and 24×). The 0.1 Hz low frequency (highpass) pole substantially attenuates the baseline component of the transthoracic impedance signal, but substantially transmits the time-varying component of the transthoracic impedance signal representing ventilation. The 2.0 Hz high frequency (lowpass) pole substantially attenuates other time-varying components of the transthoracic impedance signal that do not contribute substantial ventilation information. In particular, the lowpass pole effectively contributes to the attenuation of signal components due to the cardiac stroke signal resulting from the beating of heart 115. As described above, removal of the stroke signal is both difficult and particularly important for properly adapting the delivered pacing rate based on minute ventilation, since the stroke signal is very close in frequency to the desired ventilation signal. The lowpass pole also filters out other noise at frequencies that exceed the lowpass pole frequency.

Many different implementations of bandpass filter 420 will be suitable for use in the present invention. In one embodiment, bandpass filter 420 includes a switched-capacitor biquadratic filter stage, series-coupled with a subsequent switched-capacitor gain stage. Capacitance values of the switched-capacitor gain stage are user-programmable, thereby obtaining differing voltage gains, as described above. The output of the switched capacitor gain stage included in bandpass filter 420 is provided to the input of A/D converter 425.

Analog-to-Digital (A/D) Converter

A/D converter 425 receives the output signal of bandpass filter 420 and provides a resulting digitized output signal to highpass filter 430 of digital signal processing circuit 405. In one embodiment, A/D converter 425 is implemented as an 8-bit, successive approximation type switched-capacitor A/D converter having an input range of approximately 1 Volt. According to one aspect of the invention, A/D converter 425 provides one 8-bit digital word corresponding to each sequence of four current pulses 301–304 delivered by exciter 150. Many different implementations of A/D converter 425 will be suitable for use in the present invention. For example, a different A/D converter resolution (greater than or less than 8 bits) may be used.

Digital Signal Processing Circuit

Highpass filter 430 includes, in one embodiment, a single-pole infinite impulse response (IIR) digital filter that receives the 8-bit digital output signal from A/D converter 425, removing frequency components below its highpass cutoff frequency of approximately 0.1 Hz. Many other different embodiments of highpass filter 430 will also be suitable for use in the present invention. Highpass filter 430 advantageously further attenuates baseline dc components of the transthoracic impedance and any dc offset voltages created by A/D converter 425. The output of highpass filter 430 is provided to adaptive lowpass filter 435.

Adaptive lowpass filter 435 receives the output signal of highpass filter 430 and attenuates frequency components of the signal that exceed the lowpass cutoff frequency of adaptive lowpass filter 435. Attenuated frequencies include the cardiac stroke signal, resulting from changes in blood volume in heart 115 as it contracts during each cardiac cycle, which appears as a component of the transthoracic impedance signal. Thus, the cardiac stroke signal confounds the desired ventilation information indicating the metabolic need for adjusting pacing rate.

As described above, the component of the transthoracic impedance due to the stroke signal can be substantial. As a result, attenuation of the stroke signal is particularly important for properly adapting the delivered pacing rate based on minute ventilation. Moreover, the stroke signal is difficult to attenuate, since it is very close in frequency to the desired ventilation signal. Furthermore, the frequencies of each of the stroke and ventilation signals varies according to the patient's activity, making the stroke and ventilation signals difficult to separate.

Adaptive lowpass filter 435 provides effective attenuation of the stroke component of the processed transthoracic impedance signal received from highpass filter 430. Frequency components above a lowpass cutoff frequency are attenuated. In one embodiment, the frequency components above the lowpass cutoff frequency are attenuated by at least 30 decibels while preserving ventilation information having frequency components below the lowpass cutoff frequency. The lowpass cutoff frequency is adaptively based on a heart rate of the patient and, according to a further aspect of the invention, is independent of any breathing rate signal obtained from the patient. In one embodiment, the patient's heart rate is detected by sense amplifiers 175, and provided to adaptive lowpass filter 435, such as by controller 165, for adjusting the lowpass cutoff frequency of adaptive lowpass filter 435 accordingly. Table 1 illustrates, by way of example, but not by way of limitation, one mapping of different lowpass cutoff frequencies of adaptive lowpass filter 435 to ranges of the patient's heart rate. Other mappings may also be used.

TABLE 1

Exemplary lowpass cutoff frequencies of adaptive lowpass filter 435 based on different sensed heart rates.

| Heart Rate (beats per minute) | Lowpass cutoff frequency |
|---|---|
| <68 | 0.5 Hz |
| 68–88 | 0.75 Hz |
| >88 | 1.0 Hz |

As Table 1 illustrates, a 0.5 Hz cutoff frequency is used when the sensed heart rate is less than 68 beats per minute. When the patient's heart rate increases above 68 beats per minute, adaptive lowpass filter 435 switches its lowpass cutoff frequency to 0.75 Hz. When the patient's heart rate increases above 88 beats per minute, adaptive lowpass filter 435 switches its lowpass cutoff frequency to 1.0 Hz. Similarly, as heart rate decreases, adaptive lowpass filter 435 adjusts the lowpass cutoff frequency according to Table 1. As a result, adaptive lowpass filter 435 preserves the ventilation information at higher breathing rates (breathing rate increases together with heart rate), while continuing to attenuate the stroke signal.

The present invention bases adaptive adjustment of the lowpass cutoff frequency only on heart rate. Among other things, this reduces computational complexity and power consumption associated with monitoring the breathing rate for adjusting the lowpass cutoff frequency. This also ensures that adaptive lowpass filter 435 removes the stroke signal for all particular combinations of respiration rate and heart rate, so that pacing rate is appropriately adjusted based on minute ventilation.

In one embodiment, adaptive filter 435 uses a 4-pole Chebyshev filter that is better suited to data represented by fewer bits (e.g., 8-bit fixed point arithmetic). This conserves power and avoids instability and other potential problems of quantization. According to one aspect of the invention, adaptive lowpass filter 435 uses a state-space structure, rather than in a conventional direct form structure. The state-space structure further reduces the effects of coefficient quantization and roundoff noise. One example of such a state-space structure is described in Leland B. Jackson, "Digital Filters and Signal Processing," 2nd ed., pp. 332–340, Kluwer Academic Publishers, Boston, Mass., the disclosure of which is incorporated herein by reference.

Figure 7:
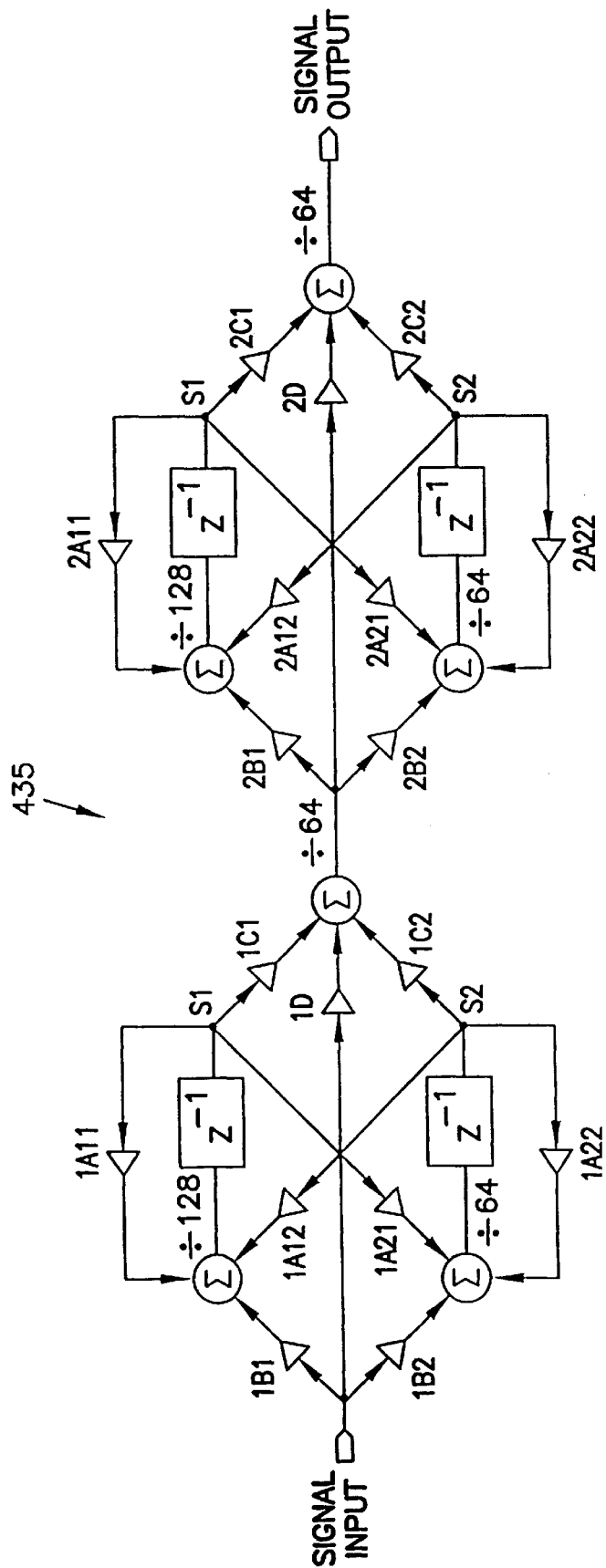
FIG. 7 is a signal flow diagram illustrating generally one embodiment of an adaptive filter.

FIG. 7 is a signal flow diagram illustrating generally one embodiment of adaptive filter 435 having a state-space topology. FIG. 7 includes scaling elements, delay elements, and summation elements. Signals output from summation elements are also scaled, as illustrated in FIG. 7. As with any DSP filter, saturation of signals at particular nodes should be avoided by adjusting the coefficients according to conventional DSP coefficient scaling techniques. One embodiment of hexadecimal values of filter coefficients is illustrated by way of example, but not by way of limitation, in Table 2.

Adaptive lowpass filter 435 outputs a signal based on transthoracic impedance and carrying ventilation information. The stroke component of the transthoracic impedance signal is substantially removed. The output of adaptive lowpass filter 435 is provided to MV calculation module 440, which calculates a minute ventilation indicated pacing rate based on the ventilation information.

TABLE 2

Exemplary Scaling Coefficients for Adaptive Filter 435

| Scaling Element (Hexadecimal) | Coefficient for 0.5 Hz Lowpass Cutoff Frequency (Hexadecimal) | Coefficient for 0.75 Hz Lowpass Cutoff Frequency (Hexadecimal) | Coefficient for 1.0 Hz Lowpass Cutoff Frequency (Hexadecimal) |
|---|---|---|---|
| 1B1 | 40 | 22 | 28 |
| 1B2 | 00 | 00 | 00 |
| 1A11 | 77 | 75 | 72 |
| 1A12 | EE | C6 | 9B |
| 1A21 | 02 | 05 | 05 |
| 1A22 | 3C | 3B | 39 |
| 1C1 | 01 | FE | FF |
| 1C2 | 40 | 60 | 7A |
| 1D | 04 | 18 | 15 |
| 2B1 | 20 | 10 | 0F |
| 2B2 | 00 | 01 | 01 |
| 2A11 | 3E | 33 | 2F |
| 2A12 | C3 | FD | FD |
| 2A21 | 01 | 0C | 18 |
| 2A22 | 3E | 33 | 2F |
| 2C1 | 00 | 02 | 06 |
| 2C2 | 40 | 3A | 3D |
| 2D | 10 | 05 | 07 |

Minute Ventilation Calculation Module

In one embodiment, MV calculation module 440 is implemented as a sequence of instructions executed on any suitable microprocessor, such as a Zilog Z80-type microprocessor. Alternatively, MV calculation module 440 is implemented as any other hardware or software configuration capable of calculating an indicated pacing rate based on ventilation information. One example of such a sequence of instructions executed on a microprocessor for calculating a minute ventilation indicated rate is described below, and illustrated in the flow chart of FIG. 8.

MV calculation module 440 receives from adaptive lowpass filter 435 a digital signal representing a time-varying transthoracic impedance. In one embodiment, the impedance signal is centered around zero, with positive values representing inhalation, and negative values representing exhalation. At step 800, the maximum (most positive) and minimum (most negative) values of the impedance signal are stored in separate storage registers. After each breath, an interrupt is provided to the microprocessor, such as upon each positive-going zero-crossing.

At step 805, the tidal volume (TV) is calculated upon receiving the interrupt. The tidal volume is obtained by reading the storage registers, and taking the difference between the maximum and minimum values of the impedance signal held for the patient's previous breath. A larger tidal volume indicates a deeper breath than a smaller tidal volume. A tidal volume data point is produced at step 805 for each breath by the patient.

At step 810, the tidal volume is integrated (i.e., the tidal volume data points are summed) for a predetermined period of time (e.g., approximately 8 seconds), obtaining a minute ventilation data point, as described in Equation 1. After each 8 second integration period, the minute ventilation data point is output, and a new integration (i.e., summation) of tidal volume commences.

Steps 815 and 820, include carrying out concurrent moving short term and long term averages, respectively. More particularly, the short term average ("STA," also referred to as a "boxcar" average) at step 815 represents, at a particular point in time, a moving average of the minute ventilation data points over the previous approximately 32 seconds. The short term average represents the present minute ventilation indication of metabolic need. Similarly, the long term average ("LTA") at step 820 represents, at a particular point in time, a moving average of the minute ventilation data points over the previous approximately 2 hours. The long term average approximates the resting state of the minute ventilation indicator. In one embodiment, the long term average at step 820 is carried out by an IIR digital filter.

At step 825, the short term and long term averages are compared. In one embodiment, this comparison involves subtracting the long term average from the short term average. The difference is optionally scaled, and used to adjust the pacing rate when the short term average exceeds the long term average. In one embodiment, the rate is adjusted according to Equation 3.

$$RATE_{MV} = LRL + K(STA - LTA) \quad (3)$$

In Equation 3, STA represents the short term average, LTA represents the long term average, K represents an optional scaling coefficient, LRL is a programmable lower rate limit to which the incremental sensor driven rate is added, and $RATE_{MV}$ is the minute ventilation indicated rate at which pacing therapy is delivered. In this embodiment, $RATE_{MV}$ is a linear function of the difference STA−LTA. Also, in this embodiment, if the value of the short term average is less than the value of the long term average, pacing therapy is delivered at the lower rate limit (LRL).

In one embodiment of the invention, more than one scaling coefficient K is used, obtaining a piecewise linear mapping of minute ventilation to the resulting minute ventilation indicated rate. For example, when the STA−LTA difference exceeds a certain threshold value, a smaller scaling coefficient K is used. This reduces the incremental increase in pacing rate for high pacing rates, when compared to the incremental increase in pacing rate for pacing rates close to the lower rate limit (LRL).

Step 825 is alternatively implemented as a ratio STA/LTA, rather than the difference STA−LTA. In one such embodiment, the rate is adjusted according to Equation 4 when STA exceeds LTA.

$$RATE_{MV} = LRL + C\left(\frac{STA}{LTA}\right) \quad (4)$$

In Equation 4, STA represents the short term average, LTA represents the long term average, C represents an optional scaling coefficient, LRL is a programmable lower rate limit to which the incremental sensor driven rate is added, and $RATE_{MV}$ is the minute ventilation indicated rate at which pacing therapy is delivered. If the value of the short term average is less than the value of the long term average, pacing therapy is delivered at the lower rate limit (LRL). In this embodiment, reduced incremental rate at high pacing rates is obtained by using more than one scaling coefficient, as described above.

Other rate modifiers can also be used to obtain a minute ventilation indicated rate. Moreover, the minute ventilation indicated rate can be combined, blended, or otherwise used in conjunction with other rate indicators, such as those derived from different sensors providing different indicators of metabolic need (e.g., acceleration). Such indicators may have different response characteristics (e.g., time lag after onset of exercise) that are advantageously combined with the minute ventilation rate indication described above.

At step 830, the indicated rate (e.g., $RATE_{MV}$) is provided to controller 165, for adjusting the rate of pacing therapy delivered by therapy circuit 170.

Minute Ventilation Calculation Alternate Embodiment

Figure 8:
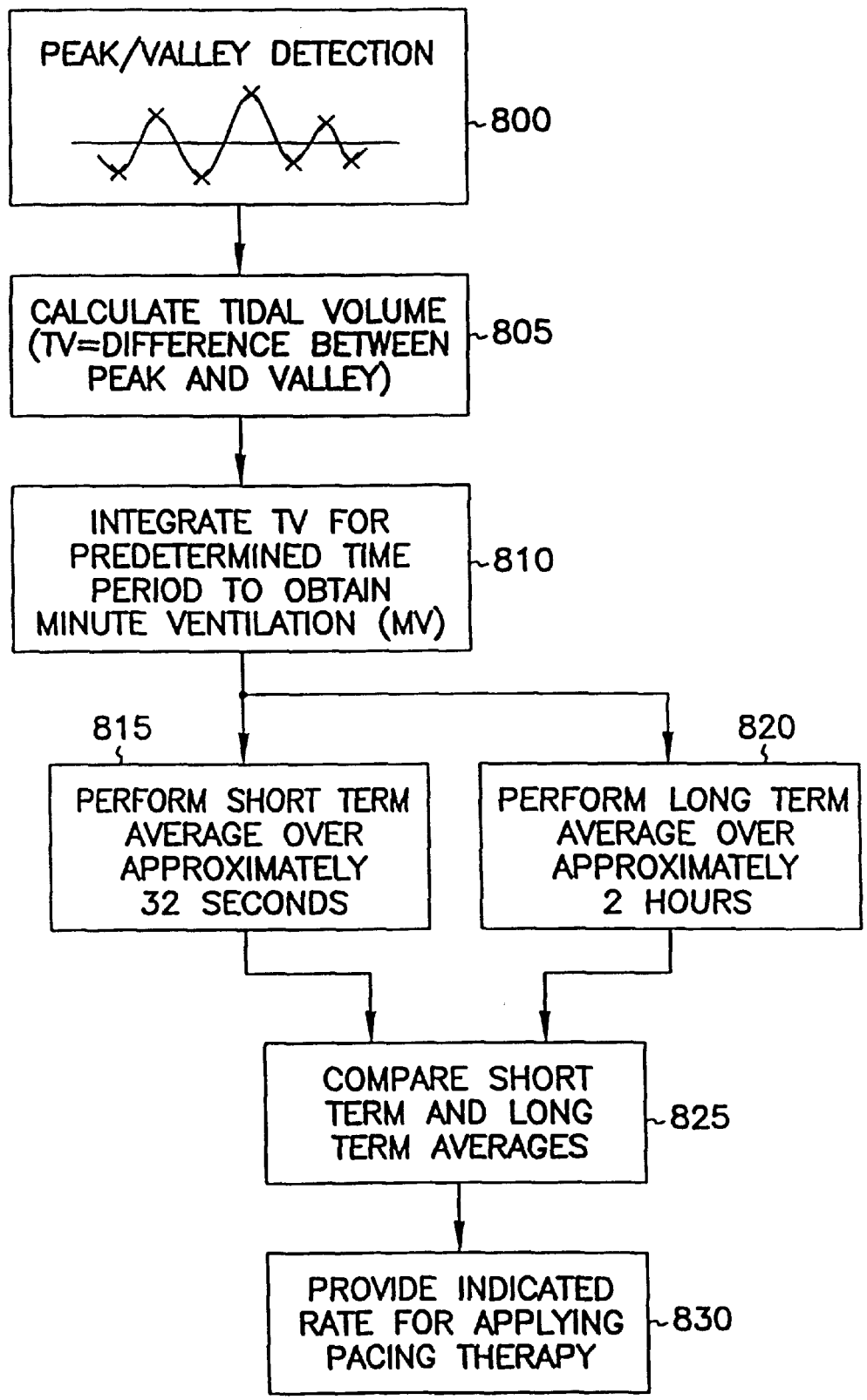
FIG. 8 is a flow chart illustrating generally one example of a sequence of steps for calculating a minute ventilation indicated rate.
Figure 9:
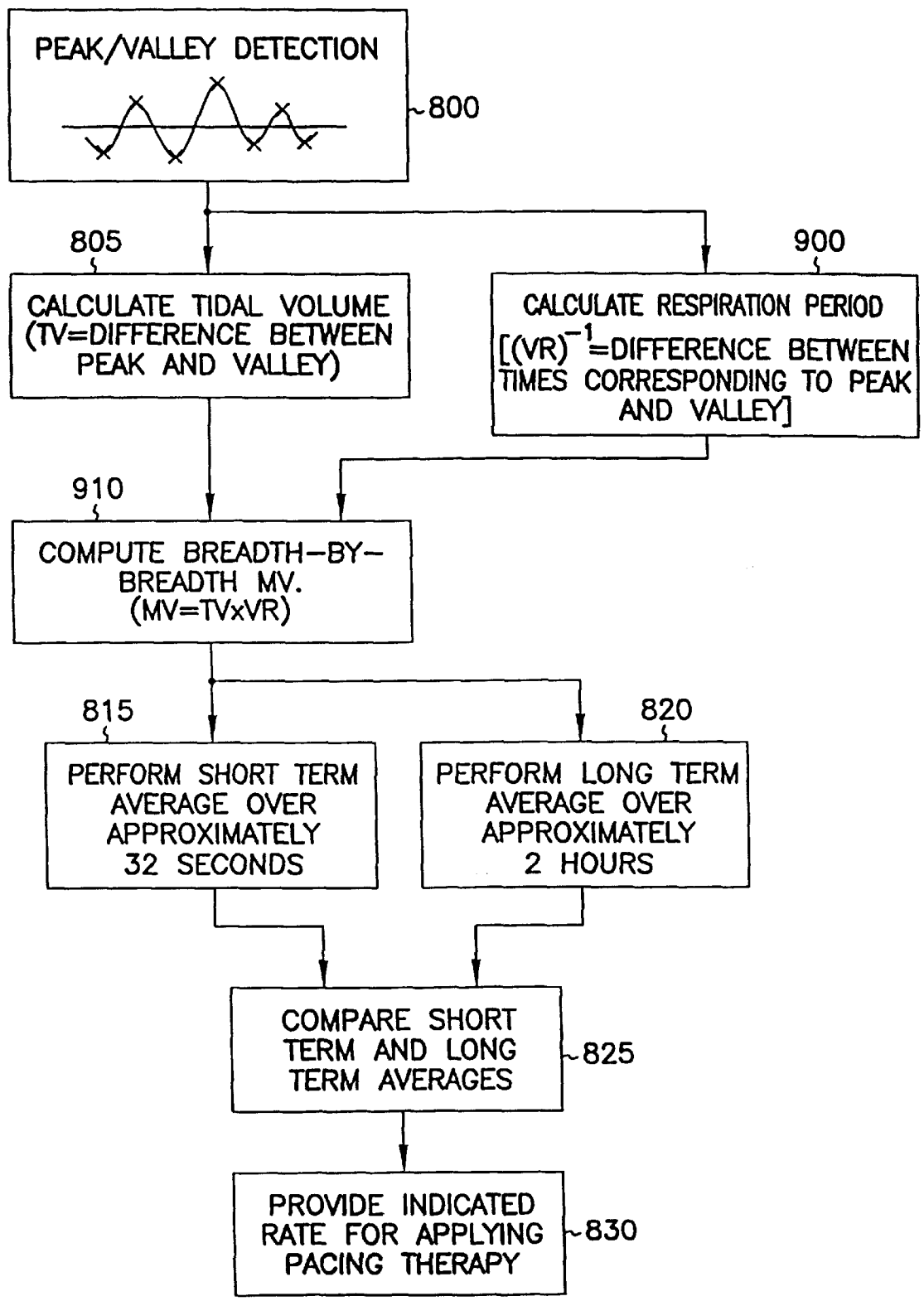
FIG. 9 is a flow chart illustrating generally a second example of a sequence of steps for calculating a minute ventilation indicated rate.

FIG. 9 is a flow chart, similar to that of FIG. 8, illustrating generally another embodiment of the invention that uses a breath-by-breath minute ventilation calculation. At step 900, time differences corresponding to the peaks and valleys of the response signal are used to obtain respiration period data points corresponding to the tidal volume data points obtained in step 805. At step 910, a breath-by-breath indication of minute ventilation is obtained, such as by dividing the tidal volume data points by the corresponding respiration period data points to obtain minute ventilation data points. The rate of delivering cardiac rhythm management therapy is then adjusted based on the minute ventilation data points, as described above with respect to FIG. 8.

Signal Processor Alternate Embodiment

Figure 10:
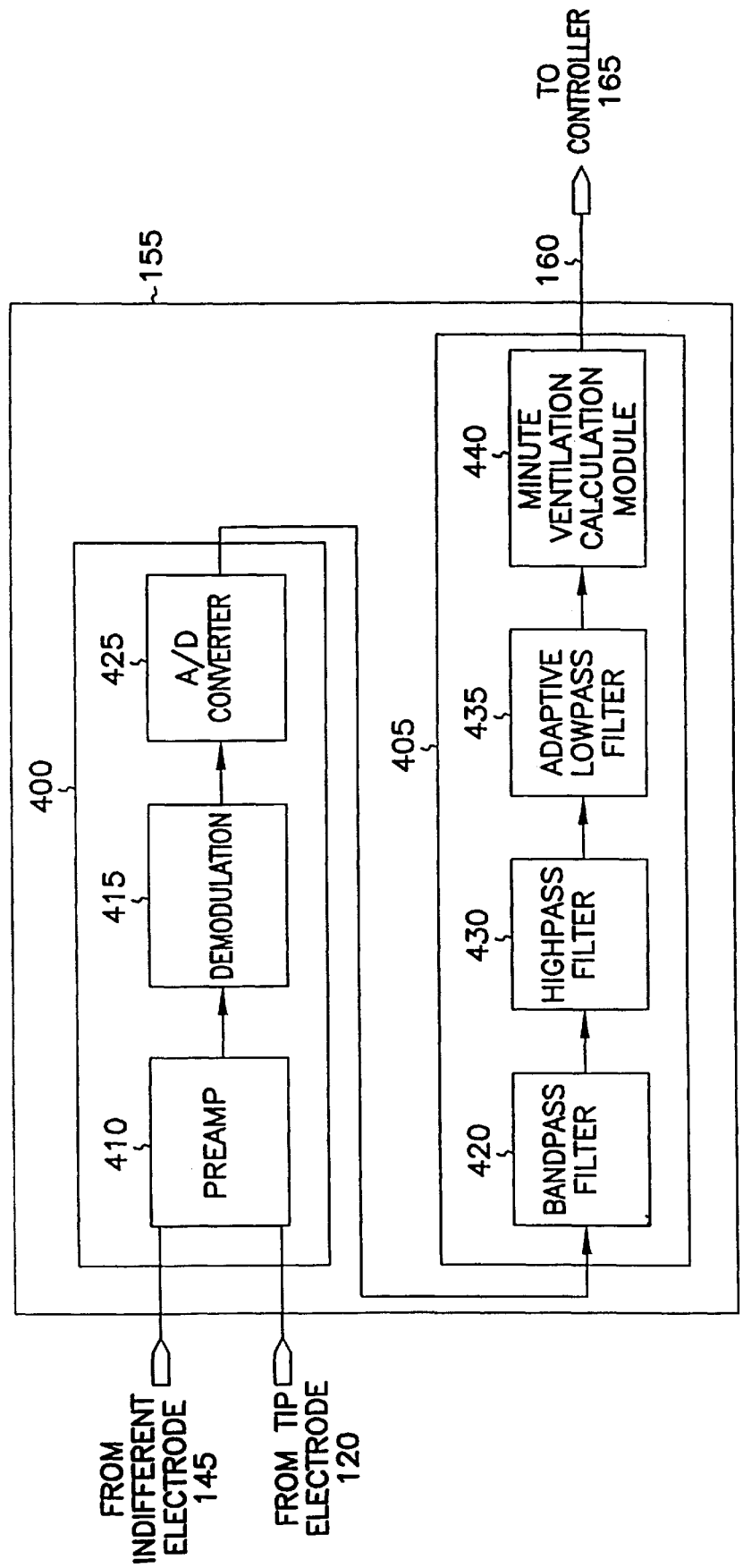
FIG. 10 is a block diagram illustrating generally an alternate embodiment of a signal processor.

The above description illustrates, by way of example, but not by way of limitation, a particular embodiment of the signal processor 155, as illustrated in FIG. 4, and methods for its use. Many other possible embodiments of signal processor 155 exist and are also included within the present invention. FIG. 10 is a block diagram illustrating generally one such variation on signal processor 155. The bandpass filter 420 of FIG. 4 is implemented digitally in the signal processor 155 of FIG. 10. Other variations are also possible without departing from the present invention.

Rate Adjustment Alternate Embodiment

The above description illustrates, by way of example, but not by way of limitation, a particular embodiment of the present invention in which ventilation information is extracted from a detected transthoracic impedance, and the rate of delivery of cardiac rhythm management therapy is adjusted based on an indicator derived from the ventilation information. However, the present invention also includes the extraction of other information (e.g., cardiac stroke information) from the transthoracic impedance, such as for adjusting the rate of delivery of cardiac rhythm management therapy based on an indicator extracted from such information. One such example is disclosed in Warren et al. U.S. Pat. No. 5,156,147 entitled, "VARIABLE RATE PACEMAKER HAVING UPPER RATE LIMIT GOVERNOR BASED ON HEMODYNAMIC PERFORMANCE," which is assigned to the assignee of the present invention, and the disclosure of which is incorporated herein by reference. Another such example is disclosed in Spinelli U.S. Pat. No. 5,235,976 entitled, "METHOD AND APPARATUS FOR MANAGING AND MONITORING CARDIAC RHYTHM MANAGEMENT USING ACTIVE TIME AS THE CONTROLLING PARAMETER," which is assigned to the assignee of the present invention, and the disclosure of which is incorporated herein by reference.

Conclusion

The present invention provides, among other things, a cardiac rhythm management device that senses transthoracic impedance and adjusts a delivery rate of the cardiac rhythm management therapy based on information extracted from the transthoracic impedance. In one embodiment, an adaptive lowpass filter removes the stroke signal from the transthoracic impedance signal while preserving the ventilation information. The adaptive filter includes a lowpass cutoff frequency that is adaptively based on the patient's heart rate, but independent of a breathing rate signal. A weighted demodulation provides filtering that enhances rejection of unwanted signals. Minute ventilation is obtained from tidal volume obtained from the ventilation information. An indicated rate is based on a difference between, or ratio of, short and long term averages of the minute ventilation information, unless noise exceeding a threshold is detected.

The present invention effectively manages the patient's heart rate based on an accurate indication of metabolic need. It provides robust operation in the presence of extraneous noise signals that confound the indication of metabolic need. It also provides low power consumption, increasing the usable life of the battery-powered implantable device.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A cardiac rhythm management device, comprising:
    an exciter, adapted to be coupled to a thorax of a patient for repeatedly delivering a multiphase stimulus thereto;
    a signal processor, including a receiver for obtaining transthoracic impedance information responsive to the stimuli;
    a demodulator, included in the signal processor, the demodulator including sampling elements for demodulating the transthoracic impedance in response to different phases of the multiphase stimulus, where the demodulator combines weighted samples of the transthoracic impedance information to attenuate unwanted signals;
    a therapy circuit, adapted to be coupled to a heart of the patient for delivering cardiac rhythm management therapy thereto; and
    a controller, coupled to the therapy circuit for adjusting a rate of delivery of the cardiac rhythm management therapy based on the transthoracic impedance.

2. The device of claim 1, in which the exciter includes a bridge switcher providing the multiphase stimulus.

3. The device of claim 2, in which the exciter includes:
    first and second capacitors, adapted for coupling the bridge switcher to the thorax of the patient; and
    a bias circuit for precharging the first and second capacitors.

4. The device of claim 1, in which the demodulator includes a switched-capacitor sampler and integrator.

5. The device of claim 4, in which the switched capacitor sampler includes capacitors that weight pulses corresponding to the phases in the multiphase stimulus.

6. The device of claim 1, further comprising:
    a noise-reversion circuit coupled to the demodulator for receiving a noise response signal in the absence of stimuli;

a noise comparator, included in the noise-reversion circuit, for comparing the noise response signal to a threshold value, and providing a resulting noise comparator output signal indicating whether the noise response signal exceeds the threshold value; and wherein the controller adjusts the rate of delivery of the cardiac rhythm management therapy independent of the transthoracic impedance if the comparator output indicates that the noise response signal exceeds the threshold value.

7. A cardiac rhythm management system, including the cardiac rhythm management device of claim 1, the cardiac rhythm management system further comprising:

an endocardial lead, carrying first and second electrodes, the lead being coupled to the cardiac rhythm management device; and a housing, carrying the cardiac rhythm management device, the housing including third and fourth electrodes.

8. The cardiac rhythm management system of claim 7, wherein the first electrode is a tip electrode, the second electrode is a ring electrode, the third electrode is a case electrode, and the fourth electrode is an indifferent electrode.

9. The cardiac rhythm management system of claim 8, wherein the indifferent electrode is carried by a header portion of the housing.

10. A cardiac rhythm management device comprising:

an exciter, adapted to be coupled to a thorax of a patient for delivering stimuli thereto;

a signal processor, including a receiver for obtaining a transthoracic impedance responsive to the stimuli, the signal processor extracting ventilation information from the transthoracic impedance, wherein the signal processor includes an adaptive lowpass filter for removing a cardiac stroke component of the transthoracic impedance signal, a cutoff frequency of the adaptive lowpass filter being adaptively based on a heart rate of the patient, the cutoff frequency of the adaptive lowpass filter being independent of a breathing rate signal from the patient;

a therapy circuit, adapted to be coupled to a heart of the patient for delivering cardiac rhythm management therapy thereto; and a controller, coupled to the therapy circuit for adjusting a rate of delivery of the cardiac rhythm management therapy based on the ventilation information.

11. The device of claim 10, in which the signal processor includes:

an analog signal processing circuit, receiving the transthoracic impedance signal and including an analog-to-digital (A/D) converter providing a responsive digital transthoracic impedance signal; and wherein the adaptive lowpass filter includes a digital 4-pole Chebyshev filter including a state-space structure.

12. The device of claim 10, wherein the controller selects the cutoff frequency of the adaptive lowpass filter to be higher when the heart activity signal indicates a higher heart rate and lower when the heart activity signal indicates a lower heart rate.

13. The device of claim 10, wherein the controller selects between a number of discrete lowpass cutoff frequencies, each lowpass cutoff frequency corresponding to a particular range of values of the heart rate.

14. The device of claim 13, wherein the controller selects the cutoff frequency of the adaptive lowpass filter at approximately 0.5 Hz, 0.75 Hz, and 1.0 Hz when the heart rate is respectively approximately less than 68 beats per minute, between 68 and 88 beats per minute, and greater than 88 beats per minute.

15. A cardiac rhythm management system, including the cardiac rhythm management device of claim 10, the cardiac rhythm management system further comprising:

an endocardial lead, carrying first and second electrodes, the lead being coupled to the cardiac rhythm management device; and a housing, carrying the cardiac rhythm management device, the housing including third and fourth electrodes.

16. The cardiac rhythm management system of claim 15, wherein the first electrode is a tip electrode, the second electrode is a ring electrode, the third electrode is a case electrode, and the fourth electrode is an indifferent electrode.

17. The cardiac rhythm management system of claim 16, wherein the indifferent electrode is carried by a header portion of the housing.

18. A cardiac rhythm management device, comprising:

an exciter, adapted to be coupled to a thorax of a patient for repeatedly delivering a multiphase stimulus thereto;

a signal processor, including a receiver for obtaining transthoracic impedance information responsive to the stimuli;

a demodulator, included in the signal processor, the demodulator including sampling elements for demodulating the transthoracic impedance in response to different phases of the multiphase stimulus and a switched-capacitor sampler and integrator, where the switched capacitor sampler includes capacitors that weight pulses corresponding to the phases in the multiphase stimulus;

a therapy circuit, adapted to be coupled to a heart of the patient for delivering cardiac rhythm management therapy thereto; and a controller, coupled to the therapy circuit for adjusting a rate of delivery of the cardiac rhythm management therapy based on the transthoracic impedance.

19. The device of claim 18, in which the exciter includes a bridge switcher providing the multiphase stimulus.

20. The device of claim 19, in which the exciter includes:

first and second capacitors, adapted for coupling the bridge switcher to the thorax of the patient; and a bias circuit for precharging the first and second capacitors.

21. The device of claim 18, further comprising:

a noise-reversion circuit coupled to the demodulator for receiving a noise response signal in the absence of stimuli;

a noise comparator, included in the noise-reversion circuit, for comparing the noise response signal to a threshold value, and providing a resulting noise comparator output signal indicating whether the noise response signal exceeds the threshold value; and wherein the controller adjusts the rate of delivery of the cardiac rhythm management therapy independent of the transthoracic impedance if the comparator output indicates that the noise response signal exceeds the threshold value.

22. A cardiac rhythm management system, including the cardiac rhythm management device of claim 18, the cardiac rhythm management system further comprising:

an endocardial lead, carrying first and second electrodes, the lead being coupled to the cardiac rhythm management device; and a housing, carrying the cardiac rhythm management device, the housing including third and fourth electrodes.

23. The cardiac rhythm management system of claim 22, wherein the first electrode is a tip electrode, the second electrode is a ring electrode, the third electrode is a case electrode, and the fourth electrode is an indifferent electrode.

24. The cardiac rhythm management system of claim 23, wherein the indifferent electrode is carried by a header portion of the housing.

25. A cardiac rhythm management device, comprising:
   an exciter, adapted to be coupled to a thorax of a patient for repeatedly delivering a multiphase stimulus thereto;
   a signal processor, including a receiver for obtaining transthoracic impedance information responsive to the stimuli;
   a demodulator, included in the signal processor, the demodulator including sampling elements for demodulating the transthoracic impedance in response to different phases of the multiphase stimulus;
   a therapy circuit, adapted to be coupled to a heart of the patient for delivering cardiac rhythm management therapy thereto;
   a noise-reversion circuit coupled to the demodulator for receiving a noise response signal in the absence of stimuli;
   a noise comparator, included in the noise-reversion circuit, for comparing the noise response signal to a threshold value, and providing a resulting noise comparator output signal indicating whether the noise response signal exceeds the threshold value; and
   a controller, coupled to the therapy circuit for adjusting a rate of delivery of the cardiac rhythm management therapy based on the transthoracic impedance, wherein the controller adjusts the rate of delivery of the cardiac rhythm management therapy independent of the transthoracic impedance if the comparator output indicates that the noise response signal exceeds the threshold value.

26. The device of claim 25, in which the exciter includes a bridge switcher providing the multiphase stimulus.

27. The device of claim 26, in which the exciter includes:
   first and second capacitors, adapted for coupling the bridge switcher to the thorax of the patient; and
   a bias circuit for precharging the first and second capacitors.

28. The device of claim 25, in which the demodulator includes a switched-capacitor sampler and integrator.

29. The device of claim 28, in which the switched capacitor sampler includes capacitors that weight pulses corresponding to the phases in the multiphase stimulus.

30. A cardiac rhythm management system, including the cardiac rhythm management device of claim 25, the cardiac rhythm management system further comprising:
   an endocardial lead, carrying first and second electrodes, the lead being coupled to the cardiac rhythm management device; and
   a housing, carrying the cardiac rhythm management device, the housing including third and fourth electrodes.

31. The cardiac rhythm management system of claim 30, wherein the first electrode is a tip electrode, the second electrode is a ring electrode, the third electrode is a case electrode, and the fourth electrode is an indifferent electrode.

32. The cardiac rhythm management system of claim 31, wherein the indifferent electrode is carried by a header portion of the housing.

33. A cardiac rhythm management device comprising:
   an exciter, adapted to be coupled to a thorax of a patient for repeatedly delivering a multiphase stimulus thereto;
   a signal processor, including a receiver for obtaining transthoracic impedance information responsive to the stimuli;
   a demodulator, included in the signal processor, the demodulator including sampling elements for demodulating the transthoracic impedance in response to different phases of the multiphase stimulus;
   a therapy circuit, adapted to be coupled to a heart of the patient for delivering cardiac rhythm management therapy thereto;
   a controller, coupled to the therapy circuit for adjusting a rate of delivery of the cardiac rhythm management therapy based on the transthoracic impedance;
   an endocardial lead, carrying first and second electrodes adapted to be implanted in the heart, the lead being coupled to the cardiac rhythm management device; and
   a housing, carrying the cardiac rhythm management device, the housing including third and fourth electrodes.

34. The cardiac rhythm management system of claim 33, wherein the first electrode is a tip electrode, the second electrode is a ring electrode, the third electrode is a case electrode, and the fourth electrode is an indifferent electrode.

35. The cardiac rhythm management system of claim 34, wherein the indifferent electrode is carried by a header portion of the housing.

36. A cardiac rhythm management device comprising:
   an exciter, adapted to be coupled to a thorax of a patient for delivering stimuli thereto;
   a signal processor, including a receiver for obtaining a transthoracic impedance responsive to the stimuli, the signal processor extracting ventilation information from the transthoracic impedance, wherein the signal processor includes an adaptive lowpass filter for removing a cardiac stroke component of the transthoracic impedance signal, a cutoff frequency of the adaptive lowpass filter being adaptively based on a heart rate of the patient, the cutoff frequency of the adaptive lowpass filter being independent of a breathing rate signal from the patient;
   a therapy circuit, adapted to be coupled to a heart of the patient for delivering cardiac rhythm management therapy thereto; and
   a controller, coupled to the therapy circuit for adjusting a rate of delivery of the cardiac rhythm management therapy based on the ventilation information, where the controller selects between a number of discrete lowpass cutoff frequencies, each lowpass cutoff frequency corresponding to a particular range of values of the heart rate.

37. The device of claim 36, wherein the controller selects the cutoff frequency of the adaptive lowpass filter at approximately 0.5 Hz, 0.75 Hz, and 1.0 Hz when the heart rate is respectively approximately less than 29 beats per minute, between 68 and 88 beats per minute, and greater than 88 beats per minute.

38. The device of claim 36, in which the signal processor includes:
   an analog signal processing circuit, receiving the transthoracic impedance signal and including an analog-to-digital (A/D) converter providing a responsive digital transthoracic impedance signal; and wherein the adaptive lowpass filter includes a digital 4-pole Chebyshev filter including a state-space structure.

39. The device of claim 36, wherein the controller selects the cutoff frequency of the adaptive lowpass filter to be higher when the heart activity signal indicates a higher heart rate and lower when the heart activity signal indicates a lower heart rate.

40. A cardiac rhythm management system, including the cardiac rhythm management device of claim 36, the cardiac rhythm management system further comprising:

an endocardial lead, carrying first and second electrodes, the lead being coupled to the cardiac rhythm management device; and a housing, carrying the cardiac rhythm management device, the housing including third and fourth electrodes.

41. The cardiac rhythm management system of claim 40, wherein the first electrode is a tip electrode, the second electrode is a ring electrode, the third electrode is a case electrode, and the fourth electrode is an indifferent electrode.

42. The cardiac rhythm management system of claim 41, wherein the indifferent electrode is carried by a header portion of the housing.

43. A cardiac rhythm management device comprising:

an exciter, adapted to be coupled to a thorax of a patient for delivering stimuli thereto;

a signal processor, including a receiver for obtaining a transthoracic impedance responsive to the stimuli, the signal processor extracting ventilation information from the transthoracic impedance, wherein the signal processor includes an adaptive lowpass filter for removing a cardiac stroke component of the transthoracic impedance signal, a cutoff frequency of the adaptive lowpass filter being adaptively based on a heart rate of the patient, the cutoff frequency of the adaptive lowpass filter being independent of a breathing rate signal from the patient;

a therapy circuit, adapted to be coupled to a heart of the patient for delivering cardiac rhythm management therapy thereto; and a controller, coupled to the therapy circuit for adjusting a rate of delivery of the cardiac rhythm management therapy based on the ventilation information;

an endocardial lead, carrying first and second electrodes, the lead being coupled to the cardiac rhythm management device; and a housing, carrying the cardiac rhythm management device, the housing including third and fourth electrodes.

44. The cardiac rhythm management system of claim 43, wherein the first electrode is a tip electrode, the second electrode is a ring electrode, the third electrode is a case electrode, and the fourth electrode is an indifferent electrode.

45. The cardiac rhythm management system of claim 44, wherein the indifferent electrode is carried by a header portion of the housing.

* * * * *

UNITED STATES PATENT AND TRADEMARK OFFICE
CERTIFICATE OF CORRECTION

PATENT NO.: 6,161,042

DATED: Dec. 12, 2000

INVENTOR(S) : Hartley et al.

It is certified that error appears in the above-identified patent and that said Letters Patent is hereby corrected as shown below:

In column 4, lines 24-25, delete the paragraph break after "patient.".

In column 13, line 13, delete "AID" and insert --A/D--, therefor.

In column 18, line 46, delete "to bc" and insert --to be--, therefor.

In column 19, line 52, delete "AID" and insert --A/D--, therefor.

In column 22, line 59, delete "29 beats" and insert --68 beats--, therefor.

Signed and Sealed this

Twenty-ninth Day of May, 2001

Attest:

NICHOLAS P. GODICI

*Attesting Officer*      *Acting Director of the United States Patent and Trademark Office*